United States Patent
Shimizu et al.

(10) Patent No.: US 10,285,914 B2
(45) Date of Patent: May 14, 2019

(54) BONDING METHOD, BONDING KIT, AND BONDING MATERIAL

(71) Applicants: Tomonao Shimizu, Tokyo (JP); Junichiro Yamagawa, Tokyo (JP)

(72) Inventors: Tomonao Shimizu, Tokyo (JP); Junichiro Yamagawa, Tokyo (JP)

(73) Assignee: TOKUYAMA DENTAL CORPORATION, Tokyo (JP)

(*) Notice: Subject to any disclaimer, the term of this patent is extended or adjusted under 35 U.S.C. 154(b) by 178 days.

(21) Appl. No.: 15/321,041

(22) PCT Filed: Jul. 3, 2015

(86) PCT No.: PCT/JP2015/069346
§ 371 (c)(1),
(2) Date: Dec. 21, 2016

(87) PCT Pub. No.: WO2016/002949
PCT Pub. Date: Jan. 7, 2016

(65) Prior Publication Data
US 2017/0156991 A1    Jun. 8, 2017

(30) Foreign Application Priority Data

| Jul. 4, 2014 | (JP) | 2014-138359 |
| Jan. 13, 2015 | (JP) | 2015-003875 |
| Feb. 2, 2015 | (JP) | 2015-018124 |
| Mar. 25, 2015 | (JP) | 2015-061978 |

(51) Int. Cl.
  *A61K 6/087* (2006.01)
  *A61K 6/00* (2006.01)
  *A61K 6/08* (2006.01)
  *A61C 19/02* (2006.01)
  *A61K 6/02* (2006.01)

(52) U.S. Cl.
  CPC ............ *A61K 6/087* (2013.01); *A61C 19/02* (2013.01); *A61K 6/00* (2013.01); *A61K 6/0023* (2013.01); *A61K 6/023* (2013.01); *A61K 6/08* (2013.01)

(58) Field of Classification Search
  CPC .................................................. A61K 6/087
  See application file for complete search history.

(56) References Cited

U.S. PATENT DOCUMENTS

| 2009/0011388 A1* | 1/2009 | Craig ............ A61K 6/0023 433/228.1 |
| 2009/0076182 A1 | 3/2009 | Tanaka et al. |
| 2010/0112518 A1* | 5/2010 | Engelbrecht ...... A61K 6/0085 433/167 |
| 2010/0304961 A1* | 12/2010 | Kimura ............ A61K 6/0023 502/160 |
| 2011/0288195 A1 | 11/2011 | Kajikawa et al. |
| 2013/0023600 A1 | 1/2013 | Kobashigawa et al. |
| 2014/0053965 A1 | 2/2014 | Ruppert et al. |

FOREIGN PATENT DOCUMENTS

| JP | 2005239560 A | 9/2005 |
| JP | 2006176488 A | 7/2006 |
| JP | 2008001624 A | 1/2008 |
| JP | 2008094732 A | 4/2008 |
| JP | 2010521257 A | 6/2010 |
| JP | 2013144778 A | 7/2013 |
| JP | 2013144783 A | 7/2013 |
| WO | 9741796 A1 | 11/1997 |

OTHER PUBLICATIONS

Gyde Fuhrmann et al., "Resin bonding to three types od polyaryletherketones (PAEKs)—Durability and influence of surface conditioning" Academy of Dental Materials 30 (2014) 357-363.
International Search Report corresponding to Application No. PCT/JP2015/069346; dated Oct. 6, 2015.
Lubica Hallmann et al., "The improvement of adhesive properties of PEEK through different pre-treatments" Applied Surface Science, (Jul. 2012) vol. 258 No. 18, 7213-7218.
Matthias Kern et al., "Influence of surface conditioning on bonding to polyetheretherketon (PEEK)", Academy of Dental Materials 28 (2012)1280-1283.
Patrick Schmidlin et al., "Effect of different surface pre-treatments and luting materials on shear bond strength to PEEK" Academy of Dental Materials 26 (2010) 553-559.
Bogna Stawarczyk et al., "Tensile bond strength of veneering resins to PEEK: Impact of different adhesives," Dental Materials Journal, vol. 32, No. 3 (Jan. 1, 2013), pp. 441-448, XP055171286.
Extended European Search Report for corresponding EP Application No. 15814198.6-1132/3165215 PCT/JP2015069346; dated Feb. 8, 2018.

* cited by examiner

*Primary Examiner* — Michael F Pepitone
(74) *Attorney, Agent, or Firm* — Cantor Colburn LLP

(57) ABSTRACT

To enable firm bonding to a member including a polyaryl ether ketone resin. A bonding method including: a bonding material applying step for applying, to the surface of a member including a polyaryl ether ketone resin, a bonding material including (A) a polymerizable monomer and (B) at least a portion of components for configuring a polymerization initiator, the content ratio of polymerizable monomers at least having two or more polymerizable functional groups in a (p2) molecule among all polymerizable monomers being 50% by mass or greater, and the content ratio of polymerizable monomers at least having one or more polymerizable functional groups and one or more functional groups capable of hydrogen bonding in a (p1h1) molecule being 5% by mass or greater; and a curing step for curing the bonding material. A bonding material and bonding kit using the bonding method.

7 Claims, No Drawings

BONDING METHOD, BONDING KIT, AND BONDING MATERIAL

CROSS REFERENCE TO RELATED APPLICATIONS

This is the U.S. national stage of application No. PCT/JP2015/069346, filed on Jul. 3, 2015. Priority under 35 U.S.C. § 119(a) and 35 U.S.C. § 365(b) is claimed from Japanese Application No. 2014-138359, filed Jul. 4, 2014; Japanese Application No. 2015-003875, filed Jan. 13, 2015; Japanese Application No. 2015-018124, filed Feb. 2, 2015; and Japanese Application No. 2015-061978, filed Mar. 25, 2015, the disclosures of which are also incorporated herein by reference.

TECHNICAL FIELD

The present invention relates to a bonding method, a bonding kit, and a bonding material.

BACKGROUND ART

Super engineering plastics are used in a wide range of applications in, for example, an electrical and electronic field, an aerospace field, an automotive industry, a medical field, and a general industrial field. Of the super engineering plastics, a polyaryletherketone resin is considered to be particularly promising for use in various fields by virtue of its excellent chemical properties and physical properties.

For example, in the field of dental treatment, there is a proposal of a technology involving using the polyaryletherketone resin as a dental material (for example, Patent Literature 1). When the polyaryletherketone resin is used as a dental material, it is necessary that the polyaryletherketone resin be firmly bonded onto tooth or another kind of dental material. As a technology for bonding a member containing the polyaryletherketone resin onto a member such as dentin or another kind of dental material as described above, there are proposed various technologies (for example, Patent Literature 2, and Non Patent Literatures 1 and 2).

CITATION LIST

Patent Literature

[PTL 1] JP 2013-144778 A
[PTL 2] JP 2010-521257 A

Non Patent Literature

[NPL 1] DENTAL MATERIALS 26 (2010) 553-559
[NPL 2] DENTAL MATERIALS 28 (2012) 1280-1283

SUMMARY OF INVENTION

Technical Problem

Meanwhile, a member containing a polyaryletherketone resin having excellent chemical properties and physical properties is widely employed in various fields without being limited to dental applications. Accordingly, there is a demand for a technology that enables firmer bonding onto the member containing a polyaryletherketone resin, irrespective of technical fields and applications.

The present invention has been made in view of the above-mentioned circumstances, and an object of the present invention is to provide a bonding method that enables firm bonding onto a member containing a polyaryletherketone resin, and a bonding kit and bonding material to be used in the bonding method.

Solution to Problem

The above-mentioned object is achieved by the present invention described below. That is, according to one embodiment of the present invention, there is provided a bonding method, including:

a bonding material-applying step of applying, onto a surface of a member containing a polyaryletherketone resin, a bonding material containing (A) polymerizable monomers and at least part of constituent components of (B) a polymerization initiator, in which in all the polymerizable monomers, a content of (p2) a polymerizable monomer having at least two or more polymerizable functional groups in a molecule is 50 mass % or more, and a content of (p1h1) a polymerizable monomer having at least one or more polymerizable functional groups and one or more hydrogen-bonding functional groups in a molecule is 5 mass % or more; and a curing step of curing the bonding material.

In a bonding method according to one embodiment of the present invention, in all the polymerizable monomers, a content of (p2h1a1) a polymerizable monomer having at least two or more polymerizable functional groups, one or more hydrogen-bonding functional groups, and one or more aromatic rings in a molecule is 20 mass % or more and 50 mass % or less.

In a bonding method according to another embodiment of the present invention, it is preferred that the bonding material contain (C) a volatile solvent.

In a bonding method according to another embodiment of the present invention, it is preferred that (C) the volatile solvent include an aprotic solvent having a ketone group.

In a bonding method according to another embodiment of the present invention, it is preferred that the bonding material contain (D) a coupling agent having at least one or more first reactive groups each capable of reacting with an inorganic compound and one or more second reactive groups each capable of reacting with an organic compound.

In a bonding method according to another embodiment of the present invention, it is preferred that (D) the coupling agent having at least one or more first reactive groups each capable of reacting with an inorganic compound and one or more second reactive groups each capable of reacting with an organic compound have a molecular structure represented by the following general formula (I).

In the general formula (I): M represents an element selected from the group consisting of metal elements and metalloid elements; X represents each of the first reactive groups and represents a reactive group selected from the group consisting of (a) a hydroxyl group, and (b) a functional group capable of forming an M-OH structure in which a hydroxyl group is directly bonded to the element M by hydrolysis; Y represents each of the second reactive groups;

and Z represents a non-reactive functional group free of a reaction with any of the organic compound and the inorganic compound.

In addition, m represents an integer of 1 or more, n represents an integer of 1 or more, l represents an integer of 0 or 1 or more, and m+n+l is an integer equal to a valence of the element M.

In a bonding method according to another embodiment of the present invention, it is preferred that: the first reactive groups X shown in the general formula (I) each include (b) the functional group capable of forming an M-OH structure in which a hydroxyl group is directly bonded to the element M by hydrolysis; and at least one kind of (A) the polymerizable monomers have an acidic group.

In a bonding method according to another embodiment of the present invention, it is preferred that the member containing a polyaryletherketone resin further contain an inorganic oxide.

In a bonding method according to another embodiment of the present invention, it is preferred that the inorganic oxide include a silicon-containing inorganic oxide.

In a bonding method according to another embodiment of the present invention, it is preferred that the hydrogen-bonding functional groups include a mercapto group.

In a bonding method according to another embodiment of the present invention, it is preferred that the mercapto group include a group generated by tautomerism of a polymerizable monomer molecule.

In a bonding method according to another embodiment of the present invention, it is preferred that: (B) the polymerization initiator include at least (Bc) a chemical polymerization initiator, and the bonding material contain part of constituent components of (Bc) the chemical polymerization initiator; and the curing step be initiated by carrying out a contact step of bringing the bonding material into contact with a polymerization auxiliary material containing a remainder constituent component of (Bc) the chemical polymerization initiator.

In a bonding method according to another embodiment of the present invention, it is preferred that the member containing a polyaryletherketone resin include a dental member.

According to one embodiment of the present invention, there is provided a bonding kit to be used at least for bonding onto a member containing a polyaryletherketone resin, the bonding kit including at least:

a bonding material containing (A) polymerizable monomers and at least part of constituent components of (B) a polymerization initiator, in which in all the polymerizable monomers, a content of (p2) a polymerizable monomer having at least two or more polymerizable functional groups in a molecule is 50 mass % or more, and a content of (p1h1) a polymerizable monomer having at least one or more polymerizable functional groups and one or more hydrogen-bonding functional groups in a molecule is 5 mass % or more; and the member containing a polyaryletherketone resin.

In a bonding kit according to another embodiment of the present invention, it is preferred that the bonding kit be for dental use.

According to one embodiment of the present invention, there is provided a bonding material to be used at least for bonding onto a member containing a polyaryletherketone resin, the bonding material containing (A) polymerizable monomers and at least part of constituent components of (B) a polymerization initiator, in which in all the polymerizable monomers, a content of (p2) a polymerizable monomer having at least two or more polymerizable functional groups in a molecule is 50 mass % or more, and a content of (p1h1) a polymerizable monomer having at least one or more polymerizable functional groups and one or more hydrogen-bonding functional groups in a molecule is 5 mass % or more.

In a bonding material according to another embodiment of the present invention, it is preferred that the bonding material be for dental use.

Advantageous Effects of Invention

According to the present invention, the bonding method that enables firm bonding onto a member containing a polyaryletherketone resin, and the bonding kit and bonding material to be used in the bonding method can be provided.

DESCRIPTION OF EMBODIMENTS

A bonding material according to this embodiment contains (A) polymerizable monomers and at least part of constituent components of (B) a polymerization initiator, in which in all the polymerizable monomers, a content of (p2) a polymerizable monomer having at least two or more polymerizable functional groups in a molecule is 50 mass % or more, and a content of (p1h1) a polymerizable monomer having at least one or more polymerizable functional groups and one or more hydrogen-bonding functional groups in a molecule is 5 mass % or more. The bonding material according to this embodiment is used at least for bonding onto a member containing a polyaryletherketone resin (hereinafter sometimes referred to as "first member"). In addition, a bonding kit according to this embodiment includes at least the bonding material according to this embodiment and a member containing a polyaryletherketone resin, and is used at least for bonding onto the member containing a polyaryletherketone resin.

In addition, a bonding method according to this embodiment includes a bonding material-applying step of applying the bonding material according to this embodiment onto a surface of the first member, and a curing step of curing the bonding material. In the bonding material-applying step, the bonding material may be applied in a state of a mixture with another composition onto the surface of the first member, and in the curing step, the bonding material may be cured in a state of a mixture with another composition. In addition, the mode in which the bonding material is applied onto the surface of the first member is not particularly limited. For example, the bonding material may be directly applied onto the surface of the first member, or after the bonding material has been applied onto the surface of another member than the first member, the bonding material may be brought into contact with the surface of the first member by bringing the other member into contact with the first member.

The first member may be any member as long as a portion thereof in the vicinity of its adherend surface to be brought into contact with the bonding material according to this embodiment for bonding contains at least a polyaryletherketone resin. In addition, in the bonding method according to this embodiment, the bonding object of the bonding material according to this embodiment may be the first member alone, or may be each of the first member and a second member.

When the bonding object is formed only of the first member, for example, one end and the other end of a jointed ring-shaped first member may be bonded onto each other through the use of the bonding material according to this embodiment. In addition, bonding may be performed in a mode in which a recessed portion, such as a hole or a groove, of a first member having formed therein the recessed portion is filled with the bonding material according to this embodiment. In this case, the recessed portion is buried, and a bonding material layer filled into the recessed portion and the inner wall surface of the recessed portion of the first member are bonded onto each other.

In addition, when the bonding object is formed of two members, i.e., the first member and the second member, the first member and the second member are bonded onto each other through the use of the bonding material according to this embodiment. In this case, the second member is not particularly limited as long as the member can be bonded onto the bonding material according to this embodiment. For example, the second member may be a member that shows a solid state from before the initiation of bonding work (hereinafter sometimes referred to as "solid state second member"), or may be a curable member that shows a paste state or a liquid state before the initiation of bonding work, and that cures during the bonding work to show a solid state after the completion of the bonding work (hereinafter sometimes referred to as "curable second member").

The solid state second member may be a member containing at least a polyaryletherketone resin in a portion in the vicinity of its adherend surface like the first member, or may be a member containing no polyaryletherketone resin in the portion in the vicinity of its adherend surface (member different from the first member).

The curable second member may be capable of functioning as a bonding material. In this case, cured matter of the bonding material according to this embodiment and cured matter of the curable second member can be firmly bonded onto each other. Besides, the curable second member may also be employed for bonding with another solid member (hereinafter sometimes referred to as "third member"). For example, when the curable second member is a member having a property of firmly bonding onto the surface of the third member, the first member and the third member can be firmly bonded by applying the bonding material according to this embodiment onto the first member, and applying the curable second member before curing onto the third member, followed by bonding. As the third member, any known solid member may be employed without any particular limitation, but in general, a member containing no polyaryletherketone resin in a portion in the vicinity of its adherend surface (member different from the first member) is preferably employed. Details of the first member, the second member, and the third member are described later.

In the bonding method according to this embodiment, the use of the bonding material according to this embodiment enables firm bonding onto the first member containing a polyaryletherketone resin. The reason why such high bonding property is obtained is not necessarily clear. However, the inventors of the present invention surmise that the reason is that the affinity between the bonding material according to this embodiment and the surface of the first member containing a polyaryletherketone resin is extremely high. That is, when the bonding material according to this embodiment is applied onto the surface of the first member containing a polyaryletherketone resin, while the bonding material containing (A) the polymerizable monomers penetrates fine unevenness present on the surface of the first member and the like to form engagement, a substantially uniform layer can be formed on the surface. Through polymerization of the layer, a uniform and firm bonding material layer can be formed.

Now, (A) the polymerizable monomers and (B) the polymerization initiator, which are essential components to be used for the bonding material according to this embodiment, and other optional components that may be used as necessary are described.

(A) Polymerizable Monomers

In the bonding material, an interaction between individual molecules constituting the bonding material, and an interaction between each of those molecules and the surface of an adherend are extremely important. In the description of the present application, in consideration of this respect, when (A) the polymerizable monomers, which are main constituent materials for the bonding material, are described, classificatory expressions with particular attention to those partial structures (kinds and numbers of functional groups) in polymerizable monomer molecules that greatly affect the above-mentioned interactions are sometimes used as necessary.

In this connection, when "(A) the polymerizable monomers" are classified on the basis of the kinds and numbers of functional groups contained in their molecules, each polymerizable monomer is expressed by combining a symbol representing the kind of a functional group necessarily contained in the molecule, and a numerical value representing the minimum number of specific functional groups necessarily contained in the molecule. That is, when a polymerizable functional group, a hydrogen-bonding functional group, and an aromatic ring are represented by symbol "p", symbol "h", and symbol "a", respectively, "p2" means a polymerizable monomer having at least two or more polymerizable functional groups in the molecule, "p1h1" means a polymerizable monomer having at least one or more polymerizable functional groups and one or more hydrogen-bonding functional groups in the molecule, "p2h1" means a polymerizable monomer having at least two or more polymerizable functional groups and one or more hydrogen-bonding functional groups in the molecule, and "p2h1a1" means a polymerizable monomer having at least two or more polymerizable functional groups, one or more hydrogen-bonding functional groups, and one or more aromatic rings in the molecule. Therefore, in the description of the present application, a classificatory expression, such as "p2", is sometimes used to express, in an abbreviated form, the kind and smallest number of functional groups that a polymerizable monomer at least has in the molecule. For example, a polymerizable monomer having at least two or more polymerizable functional groups in the molecule is sometimes expressed in an abbreviated form as "p2 type polymerizable monomer." In addition, when a classificatory expression does not contain a symbol representing a predetermined functional group, it does not matter whether the functional group in question is present or absent in the molecule of the polymerizable monomer.

A polymerizable monomer having at least one or more polymerizable functional groups in the molecule may be expressed as "p1", but the feature of having at least one or more polymerizable functional groups in the molecule is common to all the polymerizable monomers to be used in the bonding material according to this embodiment. Accordingly, in the description of the present application, when a polymerizable monomer molecule has at least one or more polymerizable functional groups in the molecule, that is, when a polymerizable monomer molecule is expressed as "p1", the expression "p1" alone is omitted.

Therefore, for example, a polymerizable monomer having two polymerizable functional groups, one hydrogen-bonding functional group, and one aromatic ring, and having no other functional group, and a polymerizable monomer having three polymerizable functional groups and two hydrogen-bonding functional groups, and having no other functional group are each classified as a p2 type polymerizable monomer, and also classified as a p1h1 type polymerizable monomer and p2h1 type polymerizable monomer. In addition, a polymerizable monomer having one polymerizable functional group, one hydrogen-bonding functional group, and one aromatic ring, and having no other functional group is not classified as a p2 type polymerizable monomer, but is classified as a p1h1 type polymerizable monomer and also classified as a p1h1a1 type polymerizable monomer.

Therefore, a polymerizable monomer identified by a specific substance name or molecular structure, such as 1,6-bis(methacrylethyloxycarbonylamino)-2,2,4-trimethylhexane, may correspond to a plurality of kinds of classificatory expressions.

Herein, (A) the polymerizable monomers contained in the bonding material according to this embodiment are each a monomer having at least one or more polymerizable functional groups in the molecule. Examples of the "polymerizable functional group" include a vinyl group, a styryl group, an allyl group, and a (meth)acryloyl group. The polymerizable functional group is preferably a radically polymerizable functional group in terms of low toxicity to a living body, high polymerization activity, and the like. Although examples of the functional group may include a vinyl group, a styryl group, and an allyl group, a (meth)acryloyl group is particularly preferred in terms of polymerization rate and safety for a living body.

In addition, the content of (p2) the polymerizable monomer having at least two or more polymerizable functional groups in the molecule in all the polymerizable monomers to be used for the bonding material needs to be 50 mass % or more, is preferably 60 mass % or more, more preferably 70 mass % or more, and may be 100 mass %. When the content of the p2 type polymerizable monomer is set to 50 mass % or more, a polymer to be obtained by polymerization between molecules of (A) the polymerizable monomers can form a sufficient network structure, resulting in an increase in strength of the bonding material layer. As a result, the strength of the bonding material that has penetrated fine unevenness present on the surface of the first member containing a polyaryletherketone resin is increased to further enhance the interaction between the polyaryletherketone resin and the bonding material layer, with the result that a high bonding property is obtained.

Further, the content of (p1h1) the polymerizable monomer having at least one or more polymerizable functional groups and one or more hydrogen-bonding functional groups in the molecule in all the polymerizable monomers to be used for the bonding material is 5 mass % or more, preferably 20 mass % or more, more preferably 30 mass % or more, still more preferably 50 mass % or more, and may be 100 mass %. When the content of the p1h1 type polymerizable monomer is set to 5 mass % or more, hydrogen bonding between the hydrogen-bonding functional groups further increases the strength of the bonding material layer. In addition, the hydrogen-bonding functional group of the p1h1 type polymerizable monomer and the ketone group of the polyaryletherketone resin interact with each other to further enhance the interaction between the polyaryletherketone resin and the bonding material layer. By virtue of those actions, a higher bonding property is obtained.

The term "hydrogen bonding" as used herein refers to a bonding interaction to be formed between a hydrogen atom (donor) electrically positively polarized by being bonded to an atom having high electronegativity (e.g., O, N, or S), and an electronegative atom (acceptor) having a lone pair of electrons. In the description of the present application, the "hydrogen-bonding functional group" is a functional group capable functioning as the donor and acceptor in the hydrogen bonding, and specifically refers to a hydroxyl group, a mercapto group (thiol group), an amino group, a urethane group, an amide group, or the like. When the hydrogen-bonding functional group is a hydroxyl group, the hydroxyl group may constitute part of an acidic group to be described later.

In addition, the hydrogen-bonding functional group may be generated by tautomerism of a polymerizable monomer molecule. As a specific example of the generation of the hydrogen-bonding functional group by tautomerism, for example, there is given a case where one hydrogen-bonding functional group (e.g., —OH or >NH) contained in a polymerizable monomer molecule disappears by tautomerism and another hydrogen-bonding functional group (—SH) is generated.

As (p2) the polymerizable monomer having at least two or more polymerizable functional groups in the molecule, a known one may be used without any limitation, and examples thereof include radically polymerizable monomers each having two or more (meth)acryloyl groups in the molecule described in the following (I) to (III).

(I) Bifunctional Radically Polymerizable Monomer 2,2-Bis(methacryloyloxyphenyl)propane, 2,2-bis[4-(3-methacryloyloxy)-2-hydroxypropoxyphenyl]propane, 2,2-bis(4-methacryloyloxyphenyl)propane, 2,2-bis(4-methacryloyloxypolyethoxyphenyl)propane, 2,2-bis(4-methacryloyloxydiethoxyphenyl)propane, 2,2-bis(4-methacryloyloxytetraethoxyphenyl)propane, 2,2-bis(4-methacryloyloxypentaethoxyphenyl)propane, 2,2-bis(4-methacryloyloxydipropoxyphenyl)propane, 2(4-methacryloyloxydiethoxyphenyl)-2(4-methacryloyloxytriethoxyphenyl)propane, 2(4-methacryloyloxydipropoxyphenyl)-2-(4-methacryloyloxytriethoxyphenyl)propane, 2,2-bis(4-methacryloyloxypropoxyphenyl)propane, 2,2-bis(4-methacryloyloxyisopropoxyphenyl)propane, ethylene glycol dimethacrylate, diethylene glycol dimethacrylate, triethylene glycol dimethacrylate, tetraethylene glycol dimethacrylate, neopentyl glycol dimethacrylate, 1,3-butanediol dimethacrylate, 1,4-butanediol dimethacrylate, 1,6-hexanediol dimethacrylate, 1,9-nonanediol dimethacrylate, glycerin dimethacrylate, bis(2-methacryloyloxyethyl) hydrogen phosphate, bis(6-methacryloyloxyhexyl) hydrogen phosphate, and acrylates corresponding to those methacrylates; diadducts obtained from adducts of vinyl monomers each having an —OH group, e.g., methacrylates, such as 2-hydroxyethyl methacrylate, 2-hydroxypropyl methacrylate, and 3-chloro-2-hydroxypropyl methacrylate, and acrylates corresponding to those methacrylates, and diisocyanate compounds, e.g., diisocyanatomethylbenzene, 4,4'-diphenylmethane diisocyanate, hexamethylene diisocyanate, trimethylhexamethylene diisocyanate, diisocyanatomethylcyclohexane, isophorone diisocyanate, and methylenebis(4-cyclohexyl isocyanate); and 1,2-bis(3-methacryloyloxy-2-hydroxypropoxy)ethyl and 1,6-bis(methacryloylethyloxycarbonylamino)-2,2,4-trimethylhexane.

(II) Trifunctional Radically Polymerizable Monomer

Methacrylates, such as trimethylolpropane trimethacrylate, trimethylolethane trimethacrylate, pentaerythritol trimethacrylate, and trimethylolmethane trimethacrylate, and acrylates corresponding to those methacrylates.

(III) Tetrafunctional Radically Polymerizable Monomer

Pentaerythritol tetramethacrylate, pentaerythritol tetraacrylate, and diadducts obtained from adducts of diisocyanate compounds, e.g., diisocyanatomethylbenzene, diisocyanatomethylcyclohexane, isophorone diisocyanate, hexamethylene diisocyanate, trimethylhexamethylene diisocyanate, methylenebis(4-cyclohexyl isocyanate), 4,4-diphenylmethane diisocyanate, and tolylene-2,4-diisocyanate, and glycidol dimethacrylate.

A plurality of kinds of those (p2) polymerizable monomers each having at least two or more polymerizable functional groups in the molecule may be used in combination as necessary.

As (p1h1) the polymerizable monomer having at least one or more polymerizable functional groups and one or more hydrogen-bonding functional groups in the molecule, a known one may be used without any limitation. As broad categories of the p1h1 type polymerizable monomer, there are given <a> a monofunctional polymerizable monomer having only one polymerizable functional group in the molecule, and <b> a polyfunctional polymerizable monomer having two or more polymerizable functional groups in the molecule, in other words, (p2h1) a polymerizable monomer having two or more polymerizable functional groups and one or more hydrogen-bonding functional groups in the molecule.

As <a> the monofunctional polymerizable monomer among the p1h1 type polymerizable monomers, known ones may be used without particular limitation, and examples thereof include methacrylates, such as 2-hydroxyethyl methacrylate, 2-hydroxypropyl methacrylate, 2-methacryloyloxyethyl dihydrogen phosphate, 2-methacryloyloxyethylphenyl hydrogen phosphate, 6-methacryloyloxyhexyl dihydrogen phosphate, 10-methacryloyloxyhexyl dihydrogen phosphate, 2-methacryloyloxyethyl-2-bromoethyl hydrogen phosphate, methacrylic acid, N-methacryloylglycine, N-methacryloylaspartic acid, N-methacryloyl-5-aminosalicylic acid, 2-methacryloyloxyethyl hydrogen succinate, 2-methacryloyloxyethyl hydrogen phthalate, 2-methacryloyloxyethyl hydrogen malate, 6-methacryloyloxyethyl-naphthalene-1,2,6-tricarboxylic acid, O-methacryloyltyrosine, N-methacryloyltyrosine, N-methacryloylphenylalanine, N-methacryloyl-p-aminobenzoic acid, N-methacryloyl-O-aminobenzoic acid, 2-methacryloyloxybenzoic acid, 3-methacryloyloxybenzoic acid, 4-methacryloyloxybenzoic acid, N-methacryloyl-5-aminosalicylic acid, N-methacryloyl-4-aminosalicylic acid, 11-methacryloyloxyundecane-1,1-dicarboxylic acid, 10-methacryloyloxydecane-1,1-dicarboxylic acid, 12-methacryloyloxydodecane-1,1-dicarboxylic acid, 6-methacryloyloxyhexane-1,1-dicarboxylic acid, 4-(2-methacryloyloxyethyl) trimellitate, 4-methacryloyloxyethyl trimellitate, 4-methacryloyloxybutyl trimellitate, 4-methacryloyloxyhexyl trimellitate, and 4-methacryloyloxydecyl trimellitate, and acrylates corresponding to those methacrylates.

As <b> the polyfunctional polymerizable monomer (p2h1 type polymerizable monomer) among the p1h1 type polymerizable monomers, known ones, including monomers each having a hydrogen-bonding functional group in the molecule among the monomers given above as examples of the p2 type polymerizable monomer, may be used without any particular limitation. Examples thereof include: 2,2-bis[4-(3-methacryloyloxy)-2-hydroxypropoxyphenyl]propane, glycerin dimethacrylate, bis(2-methacryloyloxyethyl) hydrogen phosphate, bis(6-methacryloyloxyhexyl) hydrogen phosphate, and acrylates corresponding to those methacrylates; diadducts obtained from adducts of vinyl monomers each having an —OH group, e.g., methacrylates, such as 2-hydroxyethyl methacrylate, 2-hydroxypropyl methacrylate, and 3-chloro-2-hydroxypropyl methacrylate, and acrylates corresponding to those methacrylates, and diisocyanateme compounds, e.g., diisocyanatomethylbenzene, 4,4'-diphenylmethane diisocyanate, hexamethylene diisocyanate, trimethylhexamethylene diisocyanate, diisocyanatomethylcyclohexane, isophorone diisocyanate, and methylenebis(4-cyclohexyl isocyanate); and 1,2-bis(3-methacryloyloxy-2-hydroxypropoxy)ethyl and 1,6-bis(methacryloylethyloxycarbonylamino)trimethylhexane.

The p1h1 type polymerizable monomer to be blended into the bonding material may be only a monofunctional polymerizable monomer, but is more preferably a polyfunctional polymerizable monomer (p2h1 type polymerizable monomer). In this case, the content of the p2h1 type polymerizable monomer in all the polymerizable monomers is preferably 5% or more, preferably 20 mass % or more, more preferably 30 mass % or more, still more preferably 50 mass % or more, and may be 100 mass %. When the content of the p2h1 type polymerizable monomer is set to 5 mass % or more, a higher bonding property is easily obtained than in the case of using only the monofunctional p1h1 type polymerizable monomer.

In addition, the content of (p2h1a1) a polymerizable monomer having at least two or more polymerizable functional groups, one or more hydrogen-bonding functional groups, and one or more aromatic rings in the molecule in all the polymerizable monomers is preferably 20 mass % or more and 50 mass % or less. In other words, when a polyfunctional polymerizable monomer (p2h1 type polymerizable monomer) is used as the p1h1 type polymerizable monomer and the content of the p2h1 type polymerizable monomer in all the polymerizable monomers is set to 20 mass % or more, part or all of the p2h1 type polymerizable monomer is preferably the p2h1a1 type polymerizable monomer.

When the p2h1a1 type polymerizable monomer having an aromatic ring in the molecule is used, the aromatic ring of the p2h1a1 type polymerizable monomer and the aromatic ring of the polyaryletherketone resin form a stack. In this case, the interaction between the polyaryletherketone resin contained in the first member and the bonding material layer is further enhanced, and hence a higher bonding property is obtained by virtue of the interaction.

The content of the p2h1a1 type polymerizable monomer in all the polymerizable monomers is preferably 20 mass % or more and 50 mass % or less as described above, and the lower limit value of the content is more preferably 30 mass % or more and the upper limit value of the content is more preferably 45 mass % or less. When the content is set to 20 mass % or more, the interaction between the polyaryletherketone resin contained in the first member and the bonding material layer can be enhanced. In addition, when the content is set to 50 mass % or less, the disturbance of the balance of the interaction between the aromatic ring of the polyaryletherketone resin and the aromatic ring of the p2h1a1 type polymerizable monomer due to the presence of an excess amount of aromatic rings can be suppressed.

As (p2h1a1) the polymerizable monomer having at least two or more polymerizable functional groups, one or more hydrogen-bonding functional groups, and one or more aromatic rings in the molecule, known ones, including monomers each having a hydrogen-bonding functional group and an aromatic ring in the molecule among the monomers given above as examples of the p2 type polymerizable monomer, and monomers each having an aromatic ring in the molecule among the monomers given above as examples of the p2h1 type polymerizable monomer, may be used without any particular limitation. Examples thereof include: 2,2-bis[4-(3-methacryloyloxy)-2-hydroxypropoxyphenyl]propane and an acrylate corresponding to the methacrylate; and diadducts obtained from adducts of vinyl monomers each having an —OH group, e.g., methacrylates, such as 2-hydroxyethyl methacrylate, 2-hydroxypropyl methacrylate, and 3-chloro-2-hydroxypropyl methacrylate, and acrylates corresponding to those methacrylates, and diisocyanate compounds each having an aromatic group, e.g., diisocyanatomethylbenzene and 4,4'-diphenylmethane diisocyanate.

As the hydrogen-bonding functional group of the p1h1 type polymerizable monomer, in particular, a mercapto group is preferably contained. When the bonding material contains the p1h1 type polymerizable monomer having a mercapto group, high bonding durability is more easily obtained by maintaining a high bonding property for the first member containing a polyaryletherketone resin over a long period of time. The reason why such high bonding durability is obtained is not clear, but the inventors of the present invention surmise the reason as described below.

That is, the polyaryletherketone resin is a hydrophobic material, and hence when the first member containing the polyaryletherketone resin is kept in a moist environment (e.g., in an oral cavity) for a long period of time, moisture becomes more liable to affect the bonding material at an interface between the first member and the bonding material. Then, as a result, deterioration of the bonding material is caused. It is surmised that the bonding property after keeping of the first member in a moist environment for a long period of time is thus significantly decreased. Meanwhile, when the bonding material containing the p1h1 type polymerizable monomer containing a mercapto group as the hydrogen-bonding functional group is applied onto the surface of the first member, the mercapto group of the p1h1 type polymerizable monomer containing a mercapto group as the hydrogen-bonding functional group reacts with the ketone group of the polyaryletherketone resin to form a thioacetal structure over time. The thioacetal structure is a comparatively stable linkage that, for example, has high water resistance and does not easily undergo hydrolysis. Accordingly, the linkage can be stably present between the bonding material and the first member for a long period of time. As a result, a high bonding property is exhibited from immediately after bonding, and the high bonding property can be maintained over a long period of time. It is surmised that high bonding durability is thus obtained.

In addition, the bonding material containing the p1h1 type polymerizable monomer containing a mercapto group as the hydrogen-bonding functional group is suitably used for bonding to, among the first members, a first member produced using a polyaryletherketone resin composite material containing a polyaryletherketone resin and an inorganic oxide. In this case, even higher bonding durability is easily obtained. The reason why such even higher bonding durability is obtained is not clear, but the inventors of the present invention surmise the reason as described below. First, when the first member contains the inorganic oxide, a surface acid site of the inorganic oxide allows the vicinity of the adherend surface of the first member to be brought into an acidic state. Accordingly, a reaction between the mercapto group of the p1h1 type polymerizable monomer containing a mercapto group as the hydrogen-bonding functional group, which is blended into the bonding material, and the ketone group of the polyaryletherketone resin contained in the first member is further promoted by the acid. It is surmised that the even higher bonding durability is thus obtained. Also when the first member does not contain the inorganic oxide, a similar effect is considered to be obtained by blending a p1h1 type polymerizable monomer having an acidic group in the molecule or an inorganic oxide into the bonding material. However, from the viewpoint that the vicinity of the adherend surface of the first member can be brought into an acidic state more reliably, it is surmised that the case where the inorganic oxide is blended into the first member and the p1h1 type polymerizable monomer containing a mercapto group as the hydrogen-bonding functional group is blended into the bonding material is more advantageous for obtaining high bonding durability.

A known inorganic oxide may be employed as the inorganic oxide to be blended into the polyaryletherketone resin composite material to be suitably used in combination with the bonding material containing the p1h1 type polymerizable monomer containing a mercapto group as the hydrogen-bonding functional group. However, from the viewpoint of obtaining particularly high bonding durability, the inorganic oxide is preferably silica, titania, silica-titania, or silica-zirconia, most preferably silica.

Also in the p1h1 type polymerizable monomer containing a mercapto group as the hydrogen-bonding functional group, as described above, the polymerizable functional group is particularly preferably a (meth)acryloyl group in terms of polymerization rate and safety for a living body. Therefore, the p1h1 type polymerizable monomer containing a mercapto group as the hydrogen-bonding functional group is preferably a polymerizable monomer containing a mercapto group and a (meth)acryloyl group. The polymerizable monomer containing a mercapto group and a (meth)acryloyl group may be exemplified by polymerizable monomers each having a structure obtained by substituting, with a mercapto group, a hydrogen atom or a hydroxyl group at a site other than a (meth)acryloyl group moiety in a polymerizable monomer having a (meth)acryloyl group, among the monomers given above as examples of the p2 type polymerizable monomer, the p1h1 type polymerizable monomer, and the p2h1a1 type polymerizable monomer.

As the p1h1 type polymerizable monomer containing a mercapto group as the hydrogen-bonding functional group, any monomer having one or more polymerizable functional groups and one or more mercapto groups in the molecule may be employed without any particular limitation, and specific examples thereof include compounds each having a free mercapto group as shown in the following compound I group to compound IV group, compound V, compound VI group, and compounds VII to IX.

Compound I group

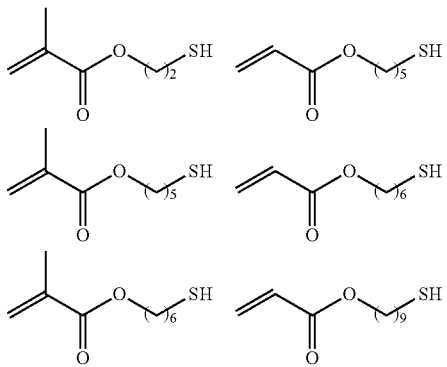

-continued
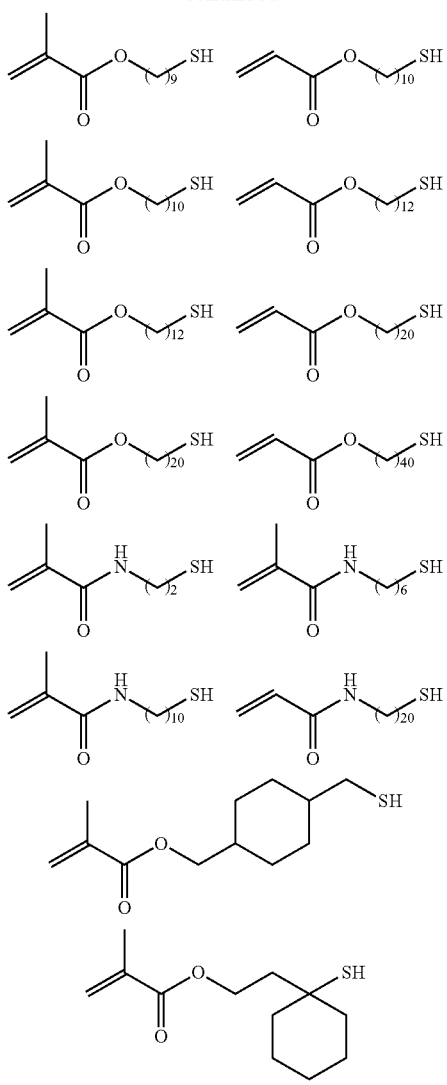
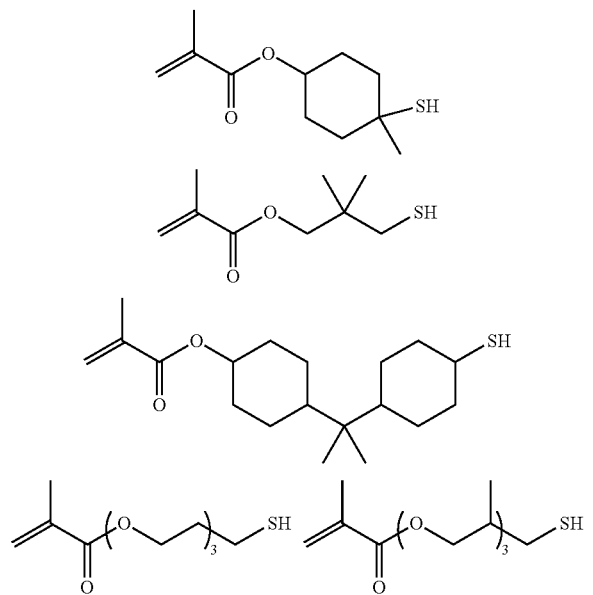
Compound II group
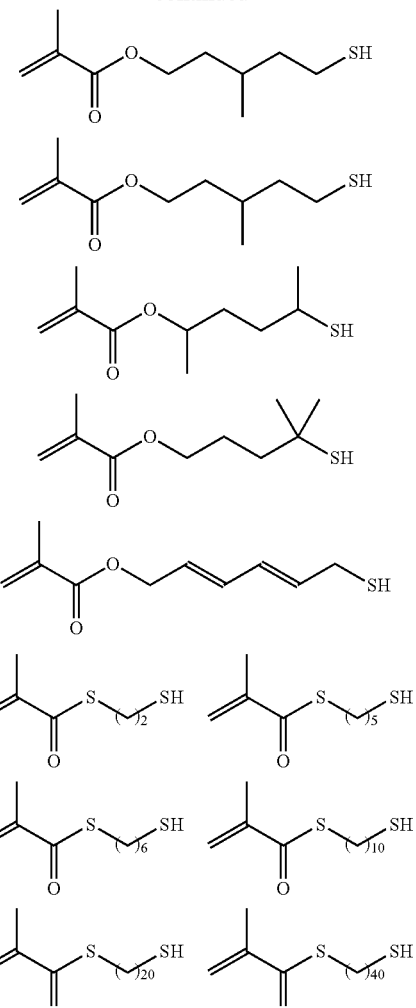
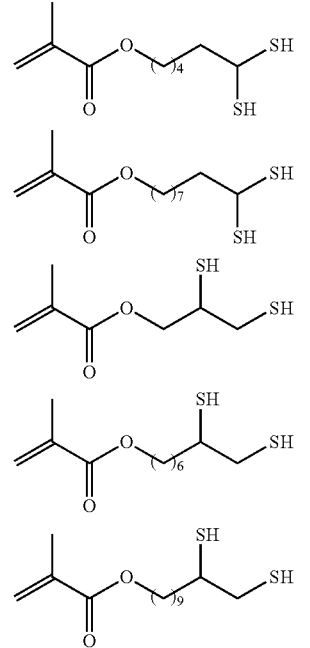
Compound III group

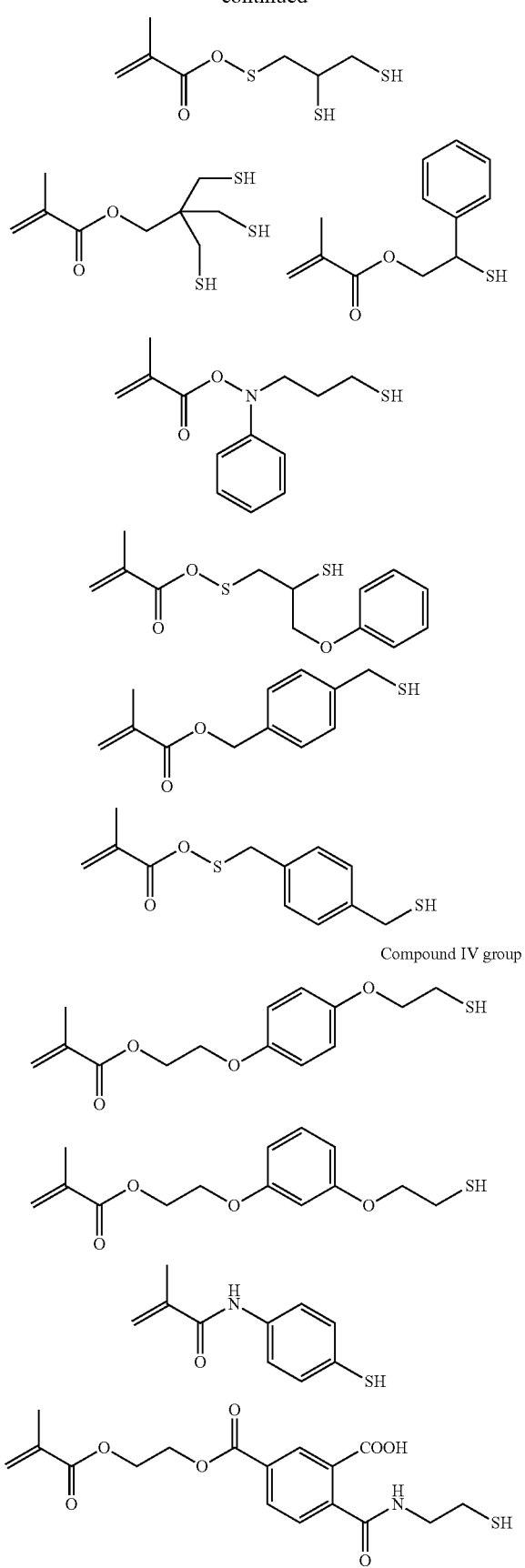

Compound IV group

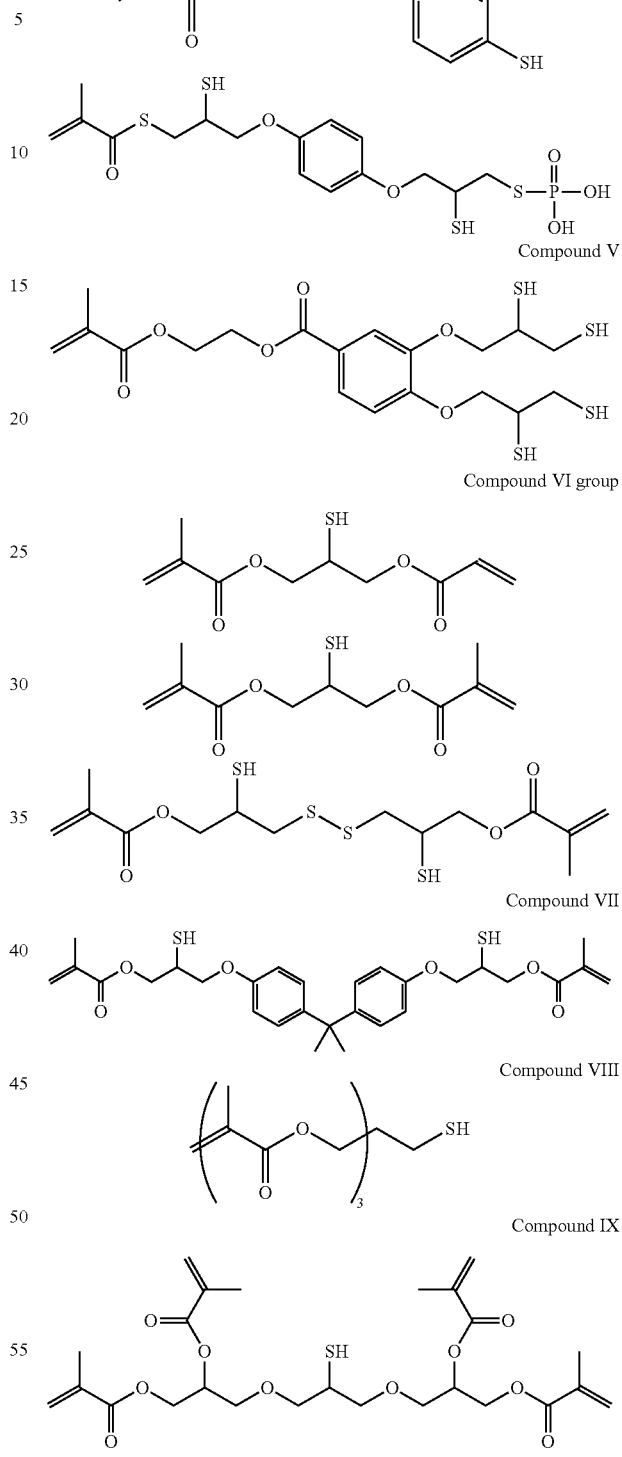

Compound V

Compound VI group

Compound VII

Compound VIII

Compound IX

The mercapto group may be a group to be generated by tautomerism of a polymerizable monomer molecule. Such polymerizable monomer capable of generating a mercapto group in the molecule by tautomerism is particularly preferably a p1h1 type polymerizable monomer. As a specific example thereof, there is given a case where in a p1h1 type polymerizable monomer having S in the molecule, a hydrogen atom of a hydrogen-bonding functional group (e.g., —OH or >NH) other than a mercapto group in the molecule is bonded to S in the molecule by tautomerism, to thereby generate a mercapto group. Such polymerizable monomer also functions in the bonding material in obtaining high bonding durability as with the p1h1 type polymerizable monomer having a (permanently present) mercapto group in the molecule as exemplified above. Examples of such polymerizable monomer include compounds as represented by the following general formulae A1 to A6.

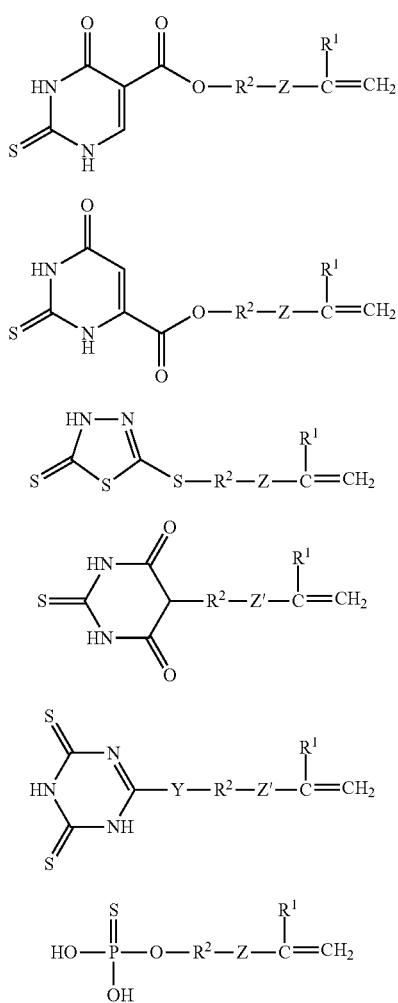

In the general formulae A1 to A6, $R^1$ represents a hydrogen atom or a methyl group. In addition, $R^2$ represents a divalent saturated hydrocarbon group having 1 to 12 carbon atoms, a —$CH_2$—$C_6H_4$—$CH_2$— group, a —$(CH_2)_o$—Si$(CH_3)_2$—O—Si$(CH_3)_2$—$(CH_2)_p$— group where o and p each represent an integer of from 1 to 5, or a —$CH_2CH_2OCH_2CH_2$— group.

In addition, Z represents an —OC(=O)— group, an —$OCH_2$— group, or an —$OCH_2$—$C_6H_4$— group (provided that in any of those Z groups, the rightmost carbon atom in the Z group is bonded to the carbon atom positioned adjacent on the right of the Z group and formed an unsaturated bond in each of the general formulae A1 to A3 and A6, and the leftmost oxygen atom in the Z group is bonded to the $R^2$ group adjacent on the left of the Z group in each of the general formulae A1 to A3 and A6). In addition, Z' represents an —OC(=O)— group (provided that the rightmost carbon atom of the —OC(=O)— group is bonded to the unsaturated carbon positioned adjacent on the right of the Z' group and formed an unsaturated bond in each of the general formulae A4 and A5, and the leftmost oxygen atom of the —OC(=O)— group is bonded to the $R^2$ group positioned adjacent on the left of the Z' group in each of the general formulae A4 and A5), a —$C_6H_4$— group, or a bonding site (herein, the case where the group Z' is a bonding site refers to a state in which the group $R^2$ and the unsaturated carbon are directly bonded to each other). Further, Y represents —S—, —O—, or —N(R')— where R' represents a hydrogen atom or an alkyl group having 1 to 5 carbon atoms.

Each of the compounds represented by the general formulae A1 to A6 is shown in a state before the generation of a mercapto group by tautomerism. In this connection, in the general formulae A1 to A5, the partial structure "—NH—C(=S)—" in each of those compounds is converted by tautomerism to "—N=C(—SH)—", to thereby generate a mercapto group. In addition, in the general formula A6, the partial structure ">P(=S)(—OH)" in the compound is converted by tautomerism to ">P(—SH)(=O)", to thereby generate a mercapto group.

Examples of the polymerizable monomers represented by the general formulae A1 to A6, each of which is capable of generating a mercapto group in the molecule by tautomerism, include compounds shown in the following compound XI group to compounds XIII group.

Compound XI group

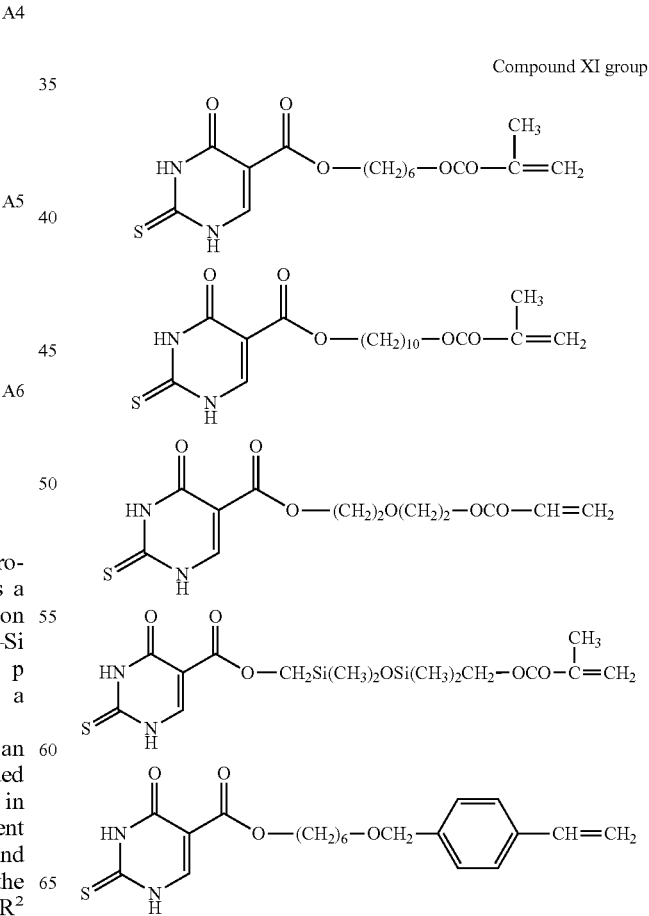

-continued

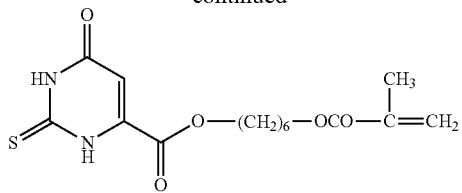

Compound XII group

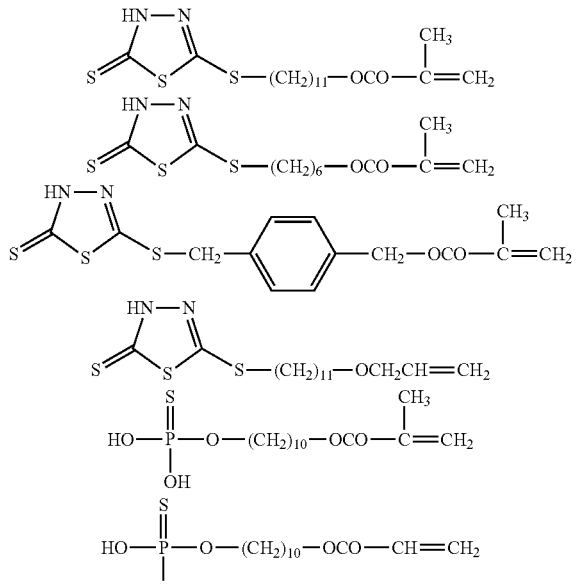

Compound XIII group

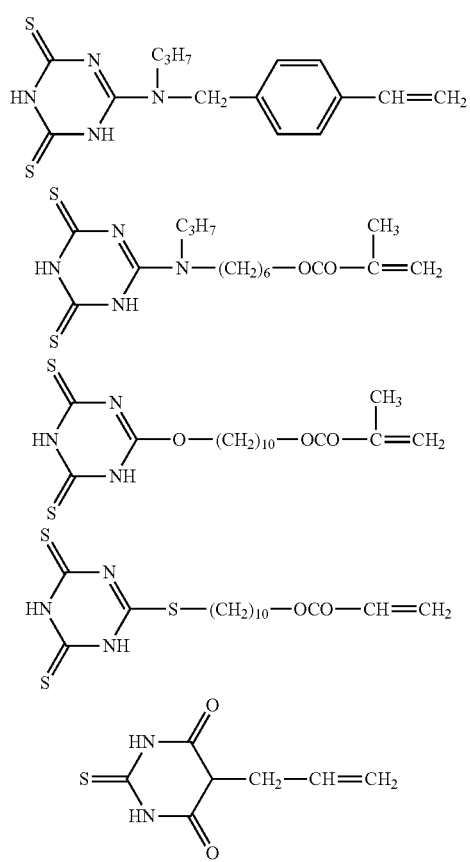

-continued

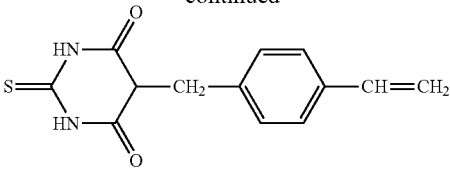

In addition, in the bonding material according to this embodiment, as a polymerizable monomer capable of generating a mercapto group in the molecule, other than the polymerizable monomer capable of generating a mercapto group in the molecule by tautomerism described above, a polymerizable monomer capable of generating a mercapto group in the molecule by some stimulus (e.g., a chemical stimulus involving a reaction with another substance, or a physical stimulus, such as photoirradiation) may also be used. In this case, the stimulus may be applied before the use of the bonding material according to this embodiment. For example, it is known that a disulfide bond is cleaved through a reaction with a reducing agent to generate a mercapto group. Accordingly, when a polymerizable monomer having a disulfide bond in the molecule is included in (A) the polymerizable monomers in the bonding material according to this embodiment, the bonding material and the reducing agent may be brought into contact or mixed with each other. In this case, in the polymerizable monomer having a disulfide bond in the molecule, the disulfide bond is cleaved by the reducing agent to generate a mercapto group in the molecule. That is, the polymerizable monomer having a disulfide bond in the molecule is converted by a chemical stimulus (reducing agent) to a p1h1 type polymerizable monomer containing a mercapto group as the hydrogen-bonding functional group.

As a mode in which the bonding material and the reducing agent are brought into contact or mixed with each other, any appropriate mode may be employed as long as the bonding property is not adversely affected, and for example, there may be employed: a) a first mode in which the polymerizable monomer having a disulfide bond in the molecule and the reducing agent are mixed before the use of the bonding material, and the resultant mixture is applied onto an adherend; b) a second mode in which a composition containing the reducing agent is applied onto an adherend surface, and then the bonding material containing the polymerizable monomer having a disulfide bond in the molecule is further applied; or c) a third mode in which the bonding material containing the polymerizable monomer having a disulfide bond in the molecule is applied onto an adherend surface, and then a composition containing the reducing agent (e.g., dental cement containing the reducing agent) is pressure-bonded onto the bonding material. Of those three modes, the first mode is preferred from the viewpoint that after contact or mixing, the p1h1 type polymerizable monomer containing a mercapto group as the hydrogen-bonding functional group is easy to generate in a sufficient amount.

In the polymerizable monomer having a disulfide bond in the molecule, the number of polymerizable functional groups contained in the molecule is not particularly limited as long as the number is 1 or more, and a hydrogen-bonding functional group or an aromatic ring may be contained, or may be not contained. In addition, as the reducing agent, any substance capable of cleaving a disulfide bond may be employed without any particular limitation.

One kind or a combination of two or more kinds of the p1h1 type polymerizable monomers each containing a mercapto group as the hydrogen-bonding functional group, or the polymerizable monomers each capable of generating a mercapto group in the molecule by tautomerism or a stimulus described above may be blended into the bonding material.

When the bonding material has blended thereinto a polymerizable monomer having a free mercapto group as the p1h1 type polymerizable monomer containing a mercapto group as the hydrogen-bonding functional group, particular attention needs to be paid to its storage stability, such as the occurrence of an addition reaction to a double bond serving as the polymerizable functional group during storage of the bonding material. With a focus on the viewpoint of the storage stability, it is preferred that the polymerizable monomer capable of generating a mercapto group by tautomerism or a stimulus be blended into the bonding material. In addition, when the polymerizable monomer capable of generating a mercapto group by a stimulus is blended into the bonding material, the operation is liable to be complicated, and moreover, in order to obtain high bonding durability, a use method sometimes needs attention so that the p1h1 type polymerizable monomer containing a mercapto group as the hydrogen-bonding functional group may be generated in a sufficient amount. With a focus on the viewpoint of the operability, it is preferred that the polymerizable monomer having a free mercapto group or the polymerizable monomer capable of generating a mercapto group by tautomerism be blended into the bonding material. Accordingly, when those respects are comprehensively considered, it is most preferred that the polymerizable monomer capable of generating a mercapto group by tautomerism be blended into the bonding material.

It is presumed that the mercapto group in each of (a) a p1h1 type polymerizable monomer having a permanently present mercapto group in the molecule, and (b) a p1h1 type polymerizable monomer in a state after the generation of a mercapto group in the molecule by tautomerism or a stimulus reacts with the ketone group of the polyaryletherketone resin contained in the first member, to thereby exhibit high bonding durability. Accordingly, in (a) the p1h1 type polymerizable monomer having a permanently present mercapto group in the molecule, steric hindrance around the mercapto group is preferably small, and in (b) the p1h1 type polymerizable monomer in a state after the generation of a mercapto group in the molecule by tautomerism or a stimulus, steric hindrance around a site at which the mercapto group has been generated is preferably small. In this connection, when the distance between the mercapto group (or the site at which the mercapto group is to be generated) and the polymerizable functional group is short, the mercapto group (or the site at which the mercapto group is to be generated) is to be present in the vicinity of a polymer main chain generated through a polymerization reaction between polymerizable monomers contained in the bonding material. Accordingly, the steric hindrance may be increased to decrease reactivity between the ketone group of the polyaryletherketone resin and the mercapto group. Therefore, it is preferred that a spacer group be present between the polymerizable functional group and the mercapto group (or the site at which the mercapto group is to be generated).

In this case, in the general formulae A1 to A6, it is preferred that $R^2$ have 4 or more atoms in its main chain, that is, represent a divalent saturated hydrocarbon group having 4 to 12 carbon atoms, a —$CH_2$—$C_6H_4$—$CH_2$— group, a —$(CH_2)_o$—$Si(CH_3)_2$—O—$Si(CH_3)_2$—$(CH_2)_p$— group where o and p each represent an integer of from 1 to 5, or a —$CH_2CH_2OCH_2CH_2$— group. Further, it is more preferred that $R^2$ have 6 or more atoms in its main chain, that is, represent a divalent saturated hydrocarbon group having 6 to 12 carbon atoms, a —$CH_2$—$C_6H_4$—$CH_2$— group, or a —$(CH_2)_o$—$Si(CH_3)_2$—O—$Si(CH_3)_2$—$(CH_2)_p$— group where o and p each represent an integer of from 1 to 5 and o+p is 3 or more. Of those, $R^2$ particularly preferably represents a divalent saturated hydrocarbon group having 6 to 12 carbon atoms. Examples of such divalent saturated hydrocarbon group having 6 to 12 carbon atoms include a 1,6-hexylene group, a 1,10-decacylene group, and a 1,11-undecacylene group.

When the polymerizable monomer capable of generating a mercapto group in the molecule by tautomerism is used, its functional group capable of generating a mercapto group by tautomerism is more preferably a thiouracil group from the viewpoint of bonding durability. That is, among the compounds of the general formulae A1 to A6, the compound of the general formula A1 or A2 is more preferred.

When the p1h1 type polymerizable monomer containing a mercapto group as the hydrogen-bonding functional group is blended into the bonding material, its content in all the polymerizable monomers is not particularly limited, but the content falls within preferably the range of from 0.005 mass % to 10 mass %, more preferably the range of from 0.01 mass % to 5 mass %, still more preferably the range of from 0.03 mass % to 1 mass %. The same applies to the case where the polymerizable monomer capable of generating a mercapto group in the molecule by tautomerism or a stimulus is blended into the bonding material.

When the content is set to 0.01 mass % or more, higher bonding durability is easily obtained. In addition, when the content is set to 10 mass % or less, deterioration of the storage stability of the bonding material can be more reliably suppressed. When the polymerizable functional group of a polymerizable monomer blended into the bonding material is a radically polymerizable functional group, during polymerization and curing of the polymerizable monomers of the bonding material by radical polymerization, the mercapto group can serve as a chain transfer agent. Accordingly, the efficiency of the radical polymerization is decreased, and particularly in the initial stage of bonding, the strength of the layer of the bonding material applied onto the surface of the first member is decreased, and the bonding property immediately after bonding may also be decreased. However, when the content is set to 10 mass % or less, even such decrease in bonding property immediately after bonding can be more reliably suppressed.

In addition, a polymerizable monomer having at least one or more acidic groups in the molecule may also be used in (A) the polymerizable monomers. In this case, the acidic group does not mean only a free acid group having —OH, such as a phosphinico group {=P(=O)OH}, a phosphono group {—P(=O)(OH)$_2$}, a carboxyl group {—C(=O)OH}, or a sulfo group (—SO$_3$H), but means such a group that an aqueous solution or aqueous suspension of a polymerizable monomer having the group shows acidity, like an acid anhydride structure obtained by dehydration condensation of two of the acidic groups having —OH exemplified above (e.g., —C(=O)—O—C(=O)—), or an acid halide group obtained by substitution of —OH of the acidic group having —OH exemplified above with a halogen (e.g., —C(=O)Cl). The acidic group preferably has a pKa of less than 5. The polymerizable monomer having at least one or more acidic groups in the molecule is classified as one kind of p1h1 type polymerizable monomer because the acidic group contains one or more hydroxyl groups, which are hydrogen-bonding functional groups. At the time of the use of the bonding material, the acid anhydride structure and the acid halide group each easily generate an acidic group containing as part thereof a hydroxyl group through a reaction with moisture in the system. Accordingly, a polymerizable monomer containing the acid anhydride structure or the acid halide group may also be classified as one kind of p1h1 type polymerizable monomer from the viewpoint of the function of the bonding material. Accordingly, in the description of the present application, both of a) a polymerizable monomer of a type having a permanently present acidic group in the molecule, and a polymerizable monomer of a type having an acid anhydride structure or an acid halide group are referred to as "p1h1 type polymerizable monomer having an acidic group in the molecule."

Specific examples of the p1h1 type polymerizable monomer having an acidic group in the molecule include polymerizable monomers each having a phosphinicooxy group or a phosphonooxy group in the molecule, such as 2-(meth)acryloyloxyethyl dihydrogen phosphate, bis(2-(meth)acryloyloxyethyl) hydrogen phosphate, 2-(meth)acryloyloxyethyl phenyl hydrogen phosphate, 10-(meth)acryloyloxydecyl dihydrogen phosphate, 6-(meth)acryloyloxyhexyl dihydrogen phosphate, bis(6-(meth)acryloyloxyhexyl) hydrogen phosphate, and 2-(meth)acryloyloxyethyl-2-bromoethyl hydrogen phosphate, and acid anhydrides and acid halides thereof.

In addition, examples thereof include polymerizable monomers each having one carboxyl group in the molecule, such as (meth)acrylic acid, N-(meth)acryloylglycine, N-(meth)acryloylaspartic acid, N-(meth)acryloyl-5-aminosalicylic acid, 2-(meth)acryloyloxyethyl hydrogen succinate, 2-(meth)acryloyloxyethyl hydrogen phthalate, 2-(meth)acryloyloxyethyl hydrogen malate, 6-(meth)acryloyloxyethylnaphthalene-1,2,6-tricarboxylic acid, O-(meth)acryloyltyrosine, N-(meth)acryloyltyrosine, N-(meth)acryloylphenylalanine, N-(meth)acryloyl-p-aminobenzoic acid, N-(meth)acryloyl-O-aminobenzoic acid, p-vinylbenzoic acid, 2-(meth)acryloyloxybenzoic acid, 3-(meth)acryloyloxybenzoic acid, 4-(meth)acryloyloxybenzoic acid, N-(meth)acryloyl-5-aminosalicylic acid, and N-(meth)acryloyl-4-aminosalicylic acid, and acid anhydrides and acid halides thereof.

In addition, examples thereof include polymerizable monomers each having a plurality of carboxyl groups or an acid anhydride group thereof in the molecule, such as 11-(meth)acryloyloxyundecane-1,1-dicarboxylic acid, 10-(meth)acryloyloxydecane-1,1-dicarboxylic acid, 12-(meth)acryloyloxydodecane-1,1-dicarboxylic acid, 6-(meth)acryloyloxyhexane-1,1-dicarboxylic acid, 2-(meth)acryloyloxyethyl-3'-methacryloyloxy-2'-(3,4-dicarboxybenzoyloxy)propyl succinate, 1,4-bis(2-(meth)acryloyloxyethyl) pyromellitate, N,O-di(meth)acryloyltyrosine, 4-(2-(meth)acryloyloxyethyl) trimellitate, 4-(meth)acryloyloxyethyl trimellitate, 4-(meth)acryloyloxybutyl trimellitate, 4-(meth)acryloyloxyhexyl trimellitate, 4-(meth)acryloyloxydecyl trimellitate, 4-acryloyloxybutyl trimellitate, 6-(meth)acryloyloxyethylnaphthalene-1,2,6-tricarboxylic acid anhydride, 6-(meth)acryloyloxyethylnaphthalene-2,3,6-tricarboxylic acid anhydride, 4-(meth)acryloyloxyethylcarbonylpropionoyl-1,8-naphthalic acid anhydride, and 4-(meth)acryloyloxyethylnaphthalene-1,8-tricarboxylic acid anhydride, and acid anhydrides and acid halides thereof.

In addition, examples thereof include polymerizable monomers each having a phosphono group in the molecule, such as vinylphosphonic acid and p-vinylbenzenephosphonic acid.

In addition, examples thereof include polymerizable monomers each having a sulfo group in the molecule, such as 2-(meth)acrylamido-2-methylpropanesulfonic acid, p-vinylbenzenesulfonic acid, and vinylsulfonic acid.

In addition to those given above as examples, monomers each containing an acidic group among the monomers given as examples of <a> the monofunctional polymerizable monomer among the p1h1 type polymerizable monomers and <b> the polyfunctional polymerizable monomer among the p1h1 type polymerizable monomers described above may also be suitably used. In addition, polymerizable monomers described as components of bonding materials disclosed in, for example, JP 54-11149 A, JP 58-140046 A, JP 59-15468 A, JP 58-173175 A, JP 61-293951 A, JP 7-179401 A, JP 8-208760 A, JP 8-319209 A, JP 10-236912 A, and JP 10-245525 A may also be suitably used.

Those p1h1 type polymerizable monomers each having an acidic group in the molecule may each be used alone, or a plurality of kinds thereof may be used in combination, and any such monomer is particularly preferably used in combination with (D) a coupling agent to be described later.

In addition, also when a chemical polymerization initiator is used as the polymerization initiator to be used for the bonding material and a fourth-period transition metal compound is used for the bonding material as part of the components of the chemical polymerization initiator, the p1h1 type polymerizable monomer having an acidic group in the molecule is suitably used. In this case, the p1h1 type polymerizable monomer having an acidic group in the molecule makes the bonding material acidic, and hence when the fourth-period transition metal compound and an organic peroxide are at least used in combination as the chemical polymerization initiator, a reaction between those substances becomes easier to activate. Details of each of those constituent components of the chemical polymerization initiator are described later.

Further, as necessary, there may be used a polymerizable monomer that does not correspond to any of the various polymerizable monomers described above, that is, a polymerizable monomer having only one polymerizable functional group in the molecule, and having none of a hydrogen-bonding functional group, an acidic group, an aromatic ring, a partial structure capable of generating a mercapto group by tautomerism, and a partial structure capable of generating a mercapto group by a stimulus such as a reducing agent. Examples of such polymerizable monomer include polymerizable monomers such as methacrylates, e.g., methyl methacrylate, ethyl methacrylate, isopropyl methacrylate, tetrahydrofurfuryl methacrylate, and glycidyl methacrylate, and acrylates corresponding to those methacrylates.

(B) Polymerization Initiator

In bonding by the bonding method according to this embodiment, when the surface of the first member and the bonding material are brought into contact with each other, the bonding material containing (A) the polymerizable monomers penetrates fine unevenness present on the surface of the first member and the like. After that, through polymerization of (A) the polymerizable monomers, the surface of the first member and the bonding material are engaged to form a uniform and firm bonding material layer, and moreover, the surface of the first member and the bonding material layer are firmly joined to each other. Accordingly, when the bonding material contains no polymerization initiator and thus (A) the polymerizable monomers cannot be cured, a uniform and firm bonding material layer cannot be formed. Therefore, at least part of the constituent components of the polymerization initiator is also blended into the bonding material according to this embodiment. As the polymerization initiator, a photopolymerization initiator, a chemical polymerization initiator, or a thermal polymerization initiator may be used, and two or more kinds of polymerization initiators may be employed in combination.

From the viewpoint that the curing of the bonding material can be simply performed, of the three kinds of polymerization initiators, a photopolymerization initiator and/or a chemical polymerization initiator are preferably used, and a photopolymerization initiator is most preferred. Now, the three kinds of polymerization initiators are described in more detail.

As the photopolymerization initiator, a known photopolymerization initiator may be used without any limitation. Typical examples of the photopolymerization initiator include photopolymerization initiators such as combinations of α-diketones and tertiary amines, combinations of acylphosphine oxides and tertiary amines, combinations of thioxanthones and tertiary amines, combinations of α-aminoacetophenones and tertiary amines, and combinations of aryl borates and photo acid generators.

The various compounds to be suitably used in the various photopolymerization initiators are exemplified below. Examples of the α-diketones include camphorquinone, benzil, α-naphthyl, acetonaphthone, naphthoquinone, p,p'-dimethoxybenzil, p,p'-dichlorobenzyl acetyl, 1,2-phenanthrenequinone, 1,4-phenanthrenequinone, 3,4-phenanthrenequinone, and 9,10-phenanthrenequinone.

Examples of the tertiary amines include N,N-dimethylaniline, N,N-diethylaniline, N,N-di-n-butylaniline, N,N-dibenzylaniline, N,N-dimethyl-p-toluidine, N,N-diethyl-p-toluidine, N,N-dimethyl-m-toluidine, p-bromo-N,N-dimethylaniline, m-chloro-N,N-dimethylaniline, p-dimethylaminobenzaldehyde, p-dimethylaminoacetophenone, p-dimethylaminobenzoic acid, ethyl p-dimethylaminobenzoate, amyl p-dimethylaminobenzoate, methyl N,N-dimethylanthranilate, N,N-dihydroxyethylaniline, N,N-dihydroxyethyl-p-toluidine, p-dimethylaminophenethyl alcohol, p-dimethylaminostilbene, N,N-dimethyl-3,5-xylidine, 4-dimethylaminopyridine, N,N-dimethyl-α-naphthylamine, N,N-dimethyl-β-naphthylamine, tributylamine, tripropylamine, triethylamine, N-methyldiethanolamine, N-ethyldiethanolamine, N,N-dimethylhexylamine, N,N-dimethyldodecylamine, N,N-dimethylstearylamine, N,N-dimethylaminoethyl methacrylate, N,N-diethylaminoethyl methacrylate, and 2,2'-(n-butylimino)diethanol. One kind of those amines may be used alone, or two or more kinds thereof may be used as a blend.

Examples of the acylphosphine oxides include benzoyldiphenylphosphine oxide, 2,4,6-trimethylbenzoyldiphenylphosphine oxide, 2,6-dimethoxybenzoyldiphenylphosphine oxide, 2,6-dichlorobenzoyldiphenylphosphine oxide, and 2,3,5,6-tetramethylbenzoyldiphenylphosphine oxide.

Examples of the thioxanthones include 2-chlorothioxanthone and 2,4-diethylthioxanthone.

Examples of the α-aminoacetophenones include 2-benzyl-dimethylamino-1-(4-morpholinophenyl)-butanone-1, 2-benzyl-diethylamino-1-(4-morpholinophenyl)-butanone-1, 2-benzyl-dimethylamino-1-(4-morpholinophenyl)-propanone-1, 2-benzyl-diethylamino-1-(4-morpholinophenyl)-propanone-1, 2-benzyl-dimethylamino-1-(4-morpholinophenyl)-pentanone-1, and 2-benzyl-diethylamino-1-(4-morpholinophenyl)-pentanone-1.

One kind of the photopolymerization initiators may be used alone, or two or more kinds thereof may be used as a mixture.

The chemical polymerization initiator is a polymerization initiator that is formed of two or more components and generates a polymerization active species at around room temperature when all the components are mixed immediately before use. Such chemical polymerization initiator is typically an amine compound/organic peroxide-based one.

Specific examples of the amine compound include aromatic amine compounds, such as N,N-dimethyl-p-toluidine, N,N-dimethylaniline, and N,N-diethanol-p-toluidine.

Typical examples of the organic peroxide include ketone peroxides, peroxyketals, hydroperoxides, dialkyl peroxides, diacyl peroxides, peroxydicarbonates, peroxyesters, and diaryl peroxides.

The organic peroxide is specifically exemplified below. Examples of the ketone peroxides include methyl ethyl ketone peroxide, cyclohexanone peroxide, methylcyclohexanone peroxide, methyl acetoacetate peroxide, and acetylacetone peroxide.

Examples of the peroxyketals include 1,1-bis(t-hexylperoxy)-3,3,5-trimethylcyclohexane, 1,1-bis(t-hexylperoxy)cyclohexane, 1,1-bis(t-butylperoxy)-3,3,5-trimethylcyclohexane, 1,1-bis(t-butylperoxy)cyclohexane, 1,1-bis(t-butylperoxy)cyclododecane, 2,2-bis(t-butylperoxy)butane, n-butyl 4,4-bis(t-butylperoxy)valerate, and 2,2-bis(4,4-di-t-butylperoxycyclohexyl)propane.

Examples of the hydroperoxides include p-methane hydroperoxide, diisopropylbenzene peroxide, 1,1,3,3-tetramethylbutyl hydroperoxide, cumene hydroperoxide, t-hexyl hydroperoxide, and t-butyl hydroperoxide.

Examples of the dialkyl peroxides include α,α-bis(t-butylperoxy)diisopropylbenzene, dicumyl peroxide, 2,5-dimethyl-2,5-bis(t-butylperoxy)hexane, t-butyl cumyl peroxide, di-t-butyl peroxide, and 2,5-dimethyl-2,5-bis(t-butylperoxy)hexane-3.

Examples of the diacyl peroxides include isobutyryl peroxide, 2,4-dichlorobenzoyl peroxide, 3,5,5-trimethylhexanoyl peroxide, octanoyl peroxide, lauroyl peroxide, stearyl peroxide, succinic acid peroxide, m-toluoyl benzoyl peroxide, and benzoyl peroxides.

Examples of the peroxydicarbonates include di-n-propyl peroxydicarbonate, diisopropyl peroxydicarbonate, bis(4-t-butylcyclohexyl) peroxydicarbonate, di-2-ethoxyethyl peroxydicarbonate, di-2-ethylhexyl peroxydicarbonate, di-2-methoxybutyl peroxydicarbonate, and di(3-methyl-3-methoxybutyl) peroxydicarbonate.

Examples of the peroxyesters include α,α-bis(neodecanoylperoxy)diisopropylbenzene, cumyl peroxyneodecanoate, 1,1,3,3-tetramethylbutyl peroxyneodecanoate, 1-cyclohexyl-1-methylethyl peroxyneodecanoate, t-hexyl peroxyneodecanoate, t-butyl peroxyneodecanoate, t-hexyl peroxypivalate, t-butyl peroxypivalate, 1,1,3,3-tetramethylbutyl peroxy-2-ethylhexanonate, 2,5-dimethyl-2,5-bis(2-ethylhexanoylperoxy)hexane, 1-cyclohexyl-1-methylethyl peroxy-2-ethylhexanonate, t-hexyl peroxy-2-ethylhexanonate, t-butyl peroxy-2-ethylhexanonate, t-butyl peroxyisobutyrate, t-hexyl peroxyisopropylmonocarbonate, t-butyl peroxymaleic acid, t-butyl peroxy-3,5,5-trimethylhexanonate, t-butyl peroxylaurate, 2,5-dimethyl-2,5-bis(m-toluoylperoxy)hexane, t-butyl peroxyisopropylmonocarbonate, t-butyl peroxy-2-ethylhexylmonocarbonate, t-hexyl peroxybenzoate, 2,5-dimethyl-2,5-bis(benzoylperoxy)hexane, t-butyl peroxyacetate, t-butyl peroxy-m-toluoylbenzoate, t-butyl peroxybenzoate, and bis(t-butyl peroxy)isophthalate.

In addition, for example, t-butyltrimethylsilyl peroxide or 3,3',4,4'-tetra(t-butylperoxycarbonyl)benzophenone may be used as the suitable organic peroxide.

The organic peroxide to be used only needs to be appropriately selected and used. One kind of the organic peroxides may be used alone, or two or more kinds thereof may be used in combination. Of those, hydroperoxides, ketone peroxides, peroxyesters, and diacyl peroxides are particularly preferred from the viewpoint of a polymerization activity. Further, of those, it is preferred to use an organic peroxide having a 10-hour half-life temperature of 60° C. or more from the viewpoint of storage stability of the bonding material.

A system in which a sulfinic acid, such as benzenesulfinic acid or p-toluenesulfinic acid and a salt thereof, is added to the initiator system formed of the organic peroxide and the amine compound, or a system in which a barbituric acid-based initiator, such as 5-butylbarbituric acid, is blended in the initiator system may also be used without any problem.

In addition, an aryl borate compound/acidic compound-based polymerization initiator utilizing such a phenomenon that an aryl borate compound is decomposed by an acid to generate a radical may also be used.

The aryl borate compound is not particularly limited, and a known compound may be used as long as the compound has at least one boron-aryl bond in the molecule. Of those, it is preferred to use an aryl borate compound having 3 or 4 boron-aryl bonds in one molecule in consideration of storage stability, and it is more preferred to use an aryl borate compound having 4 boron-aryl bonds from the viewpoints of handling and easy synthesis and availability.

Examples of the aryl borate compound having 3 boron-aryl bonds in one molecule may include sodium salts, lithium salts, potassium salts, magnesium salts, tetrabutylammonium salts, tetramethylammonium salts, tetraethylammonium salts, tributylamine salts, triethanolamine salts, methylpyridinium salts, ethylpyridinium salts, butylpyridinium salts, methylquinolinium salts, ethylquinolinium salts, or butylquinolinium salts of a monoalkyltriphenylboron, a monoalkyltris(p-chlorophenyl)boron, a monoalkyltris(p-fluorophenyl)boron, a monoalkyltris(3,5-bistrifluoromethyl)phenylboron, a monoalkyltris[3,5-bis(1,1,1,3,3,3-hexafluoro-2-methoxy-2-propyl)phenyl]boron, a monoalkyltris(p-nitrophenyl)boron, a monoalkyltris(m-nitrophenyl)boron, a monoalkyltris(p-butylphenyl)boron, a monoalkyltris(m-butylphenyl)boron, a monoalkyltris(p-butyloxyphenyl)boron, a monoalkyltris(m-butyloxyphenyl)boron, a monoalkyltris(p-octyloxyphenyl)boron, and a monoalkyltris(m-octyloxyphenyl)boron (provided that the alkyl is any one of n-butyl, n-octyl, and n-dodecyl in each of the compounds).

Examples of the aryl borate compound having 4 boron-aryl bonds in one molecule may include sodium salts, lithium salts, potassium salts, magnesium salts, tetrabutylammonium salts, tetramethylammonium salts, tetraethylammonium salts, tributylamine salts, triethanolamine salts, methylpyridinium salts, ethylpyridinium salts, butylpyridinium salts, methylquinolinium salts, ethylquinolinium salts, or butylquinolinium salts of tetraphenylboron, tetrakis(p-chlorophenyl)boron, tetrakis(p-fluorophenyl)boron, tetrakis(3,5-bistrifluoromethyl)phenylboron, tetrakis[3,5-bis(1,1,1,3,3,3-hexafluoro-2-methoxy-2-propyl)phenyl]boron, tetrakis(p-nitrophenyl)boron, tetrakis(m-nitrophenyl)boron, tetrakis(p-butylphenyl)boron, tetrakis(m-butylphenyl)boron, tetrakis(p-butyloxyphenyl)boron, tetrakis(m-butyloxyphenyl)boron, tetrakis(p-octyloxyphenyl)boron, and tetrakis(m-octyloxyphenyl)boron (provided that the alkyl is any one of n-butyl, n-octyl, or n-dodecyl in each of the compounds).

The various aryl borate compounds exemplified above may be used in combination of two or more kinds thereof.

The aryl borate compound/acidic compound-based polymerization initiator is also suitably used in combination with an organic peroxide and/or a transition metal compound. The organic peroxide is as described above. The transition metal compound is suitably a +IV-valent and/or +V-valent vanadium compound. Specific examples of the +IV-valent and/or +V-valent vanadium compound include divanadium(IV) tetroxide, vanadium(IV) oxide acetylacetonate, vanadyl(IV) oxalate, vanadyl(IV) sulfate, oxobis(1-phenyl-1,3-butanedionato)vanadium(IV), bis(maltolato)oxovanadium(IV), vanadium(V) petoxide, sodium metavanadate(V), and ammonium metavanadate(V).

In addition, there is also given a transition metal compound/organic peroxide-based chemical polymerization initiator. Specific examples of the transition metal compound include: vanadium compounds, such as divanadium(IV) tetroxide, vanadium(IV) oxide acetylacetate, vanadyl(IV) oxalate, vanadyl(IV) sulfate, oxobis(1-phenyl-1,3-butanedionato)vanadium(IV), bis(maltolato)oxovanadium(IV), vanadium(V) pentoxide, sodium metavanadate(V), and ammonium metavanadate(V); scandium compounds, such as scandium(III) iodide; titanium compounds, such as titanium(IV) chloride and titanium(IV) tetraisopropoxide; chromium compounds, such as chromium(II) chloride, chromium(III) chloride, chromic acid, and chromates; manganese compounds, such as manganese(II) acetate and manganese(II) naphthenate; iron compounds, such as iron(II) acetate, iron(II) chloride, iron(III) acetate, and iron(III) chloride; cobalt compounds, such as cobalt(II) acetate and cobalt(II) naphthenate; nickel compounds, such as nickel(II) chloride; copper compounds, such as copper(I) chloride, copper(I) bromide, copper(II) chloride, and copper(II) acetate; and zinc compounds, such as zinc(II) chloride and zinc(II) acetate. Of those transition metal compounds, a +IV-valent and/or +V-valent vanadium compound is preferably used because of, for example, the ease with which a high bonding property is obtained. Examples of the organic peroxide include those given above.

In addition, as the chemical polymerization initiator, a radically polymerizable chemical polymerization initiator using a redox reaction formed of an oxidizing agent and a reducing agent may also be suitably used. For example, the above-mentioned amine compound/organic peroxide-based chemical polymerization initiator is also one kind of the chemical polymerization initiator using a redox reaction formed of an oxidizing agent and a reducing agent.

Examples of the oxidizing agent of the chemical polymerization initiator using a redox reaction include an inorganic peroxide and an organic peroxide. Specific examples of the inorganic peroxide include sodium persulfate, potassium persulfate, aluminum persulfate, ammonium persulfate, potassium chlorate, potassium bromate, and potassium superphosphate. In addition, as the organic peroxide, an organic peroxide having a 10-hour half-life temperature of 60° C. or more described below, among the organic peroxides to be used for the above-mentioned amine compound/organic peroxide-based chemical polymerization initiator, may be suitably employed in terms of the storage stability of the bonding material.

That is, examples of such organic peroxide include: hydroperoxides, such as p-methane hydroperoxide, diisopropylbenzene peroxide, 1,1,3,3-tetramethylbutyl hydroperoxide, cumene hydroperoxide, and t-butyl hydroperoxide; peroxyesters, such as 1,1,3,3-tetramethylbutyl peroxy-2-ethylhexanoate, 2,5-dimethyl-2,5-bis(2-ethylhexanoylperoxy)hexane, t-hexyl peroxy-2-ethylhexanoate, t-butyl peroxy-2-ethylhexanoate, t-butyl peroxyisobutyrate, t-hexyl peroxyisopropyl monocarbonate, t-butylperoxymaleic acid, t-butyl peroxy-3,5,5-trimethylhexanoate, t-butyl peroxylaurate, t-butyl peroxyisopropyl monocarbonate, t-butyl peroxy-2-ethylhexyl monocarbonate, t-hexyl peroxybenzoate, 2,5-dimethyl-2,5-bis(benzoylperoxy)hexane, t-butyl peroxyacetate, t-butyl peroxybenzoate, and bis(t-butylperoxy) isophthalate; and diacyl peroxides, such as octanoyl peroxide, lauroyl peroxide, succinic acid peroxide, m-toluoylbenzoyl peroxide, and benzoyl peroxide.

In addition, t-butyltrimethylsilyl peroxide is also given as an example of the organic peroxide having a 10-hour half-life temperature of 60° C. or more.

Examples of the reducing agent of the chemical polymerization initiator using a peroxide as the oxidizing agent of the redox reaction include an amine compound, a sulfinic acid compound, a thiourea compound, an oxime compound, and a transition metal compound.

Specific examples of the amine compound include aromatic amine compounds, such as N,N-dimethyl-p-toluidine, N,N-dimethylaniline, and N,N-diethanol-p-toluidine.

A sulfinic acid compound or a salt thereof may be used as the sulfinic acid compound, and specific examples thereof include p-toluenesulfinic acid, sodium p-toluenesulfinate, potassium p-toluenesulfinate, lithium p-toluenesulfinate, calcium p-toluenesulfinate, benzenesulfinic acid, sodium benzenesulfinate, potassium benzenesulfinate, lithium benzenesulfinate, calcium benzenesulfinate, 2,4,6-trimethylbenzenesulfinic acid, sodium 2,4,6-trimethylbenzenesulfinate, potassium 2,4,6-trimethylbenzenesulfinate, lithium 2,4,6-trimethylbenzenesulfinate, calcium 2,4,6-trimethylbenzenesulfinate, 2,4,6-triethylbenzenesulfinic acid, sodium 2,4,6-triethylbenzenesulfinate, potassium 2,4,6-triethylbenzenesulfinate, lithium 2,4,6-triethylbenzenesulfinate, calcium 2,4,6-triethylbenzenesulfinate, 2,4,6-triisopropylbenzenesulfinic acid, sodium 2,4,6-triisopropylbenzenesulfinate, potassium 2,4,6-triisopropylbenzenesulfinate, lithium 2,4,6-triisopropylbenzenesulfinate, and calcium 2,4,6-triisopropylbenzenesulfinate. Of those, sodium p-toluenesulfinate, sodium benzenesulfinate, and sodium 2,4,6-triethylbenzenesulfinate are preferred.

Examples of the thiourea compound include thiourea, methylthiourea, ethylthiourea, N,N'-dimethylthiourea, N,N'-diethylthiourea, N,N'-di-n-propylthiourea, N,N'-dicyclohexylthiourea, trimethylthiourea, triethylthiourea, tri-n-propylthiourea, tricyclohexylthiourea, tetramethylthiourea, tetraethylthiourea, tetra-n-propylthiourea, tetracyclohexylthiourea, and 1-(2-pyridyl)-2-thiourea.

Examples of the oxime compound include methyl ethyl ketone oxime, methyl isobutyl ketone oxime, acetophenone oxime, and P,P'-dibenzoylquinone dioxime.

As the transition metal compound, a fourth-period transition metal compound may be particularly suitably used. The fourth-period transition metal compound refers to a compound of a metal of any of Groups 3 to 12 in the fourth period of the periodic table, specifically, a metal compound of each of scandium (Sc), titanium (Ti), vanadium (V), chromium (Cr), manganese (Mn), iron (Fe), cobalt (Co), nickel (Ni), copper (Cu), and zinc (Zn). The above-mentioned transition metal elements may each adopt a plurality of valences, and any fourth-period transition metal compound capable of serving as the reducing agent with a valence that allows its stable presence may be blended into the bonding material according to this embodiment. Typical specific examples of such compound include: +IV-valent vanadium compounds, such as divanadium(IV) tetroxide, vanadium(IV) oxide acetylacetonate, vanadyl(IV) oxalate, vanadyl(IV) sulfate, oxobis(1-phenyl-1,3-butanedionato)vanadium(IV), and bis(maltolato)oxovanadium(IV); +II-valent chromium compounds, such as chromium(II) chloride; +II-valent manganese compounds, such as manganese(II) acetate and manganese(II) naphthenate; +II-valent iron compounds, such as iron(II) acetate, iron(II) chloride, and iron (II) sulfate; +II-valent cobalt compounds, such as cobalt(II) acetate and cobalt(II) naphthenate; +II-valent nickel compounds, such as nickel naphthenate and nickel(II) chloride; and +I-valent copper compounds, such as copper(I) chloride and copper(I) bromide.

For each of the oxidizing agent and the reducing agent, two or more kinds of agents may be used in combination.

In addition, examples of the thermal polymerization initiator include: peroxides, such as benzoyl peroxide, p-chlorobenzoyl peroxide, tert-butyl peroxy-2-ethylhexanoate, tert-butyl peroxydicarbonate, and diisopropyl peroxydicarbonate; azo compounds, such as azobisisobutyronitrile; boron compounds, such as tributylborane, tributylborane partial oxide, sodium tetraphenylborate, sodium tetrakis(p-fluorophenyl)borate, and triethanolamine tetraphenylborate; barbituric acids, such as 5-butylbarbituric acid and 1-benzyl-5-phenylbarbituric acid; and sulfinates, such as sodium benzenesulfinate and sodium p-toluenesulfinate.

The blending amount of any such polymerization initiator in the bonding material falls within the range of preferably from 0.01 part by mass to 10 parts by mass, more preferably from 0.1 part by mass to 8 parts by mass with respect to 100 parts by mass of (A) the polymerizable monomers. When the blending amount of the polymerization initiator is less than 0.01 part by mass, in particular, immediately after bonding, the curing of the bonding material may be insufficient, resulting in a decrease in strength of the bonding material layer. Meanwhile, when the blending amount of the polymerization initiator is more than 10 parts by mass, there is a risk in that increased amounts of a polymerization initiator remaining unreacted and a residue of a reacted polymerization initiator may adversely affect the interaction between the first member containing a polyaryletherketone resin and the bonding material layer, to thereby cause a decrease particularly in long-term bonding property.

At least part of the constituent components of the polymerization initiator is blended into the bonding material according to this embodiment. In this case, any one of the following modes may be selected: a) a first mode in which only part of the constituent components of the polymerization initiator is blended into the bonding material; and b) a second mode in which all constituent components of the polymerization initiator are blended into the bonding material.

Which of the first mode and the second mode is selected may be appropriately determined depending on various conditions of the bonding, such as the bonding method, the composition and shape of the bonding object, such as the first member, to be used in the bonding, and the kind and composition of the polymerization initiator to be used. However, when a photopolymerization initiator or a thermal polymerization initiator is used as the polymerization initiator, it is generally preferred that the second mode be adopted. Meanwhile, when a chemical polymerization initiator is used as the polymerization initiator, any one of the first mode and the second mode may be appropriately adopted.

In this connection, in the case of using at least a chemical polymerization initiator as (B) the polymerization initiator, when the second mode is adopted, the bonding material according to this embodiment contains a first material containing part of the constituent components (first component) of the chemical polymerization initiator, and a second material containing the remainder constituent component (second component) of the chemical polymerization initiator. That is, the bonding material as a whole, which contains the first material and the second material, contains all the components of the chemical polymerization initiator. In this case, the first material and the second material are mixed immediately before the use of the bonding material. In addition, the constituent components of the bonding material other than the chemical polymerization initiator are blended in appropriately divided portions into the first material and the second material. For example, the constituent components of the bonding material other than the chemical polymerization initiator may each be blended in equal amounts into the first material and the second material.

In addition, in the case of using at least a chemical polymerization initiator as (B) the polymerization initiator, when the first mode is adopted, a bonding material containing (A) the polymerizable monomers and part of the constituent components (first component) of the chemical polymerization initiator is used as the bonding material according to this embodiment. In addition, the remainder constituent component (second component) of the chemical polymerization initiator is blended into a polymerization auxiliary material. In this case, it is appropriate that a contact step of bringing the bonding material and the polymerization auxiliary material into contact with each other be carried out. When the contact step is carried out, a polymerization reaction of (A) the polymerizable monomers contained in the bonding material is initiated, and thus the curing step is initiated and proceeds. The "bringing the bonding material and the polymerization auxiliary material into contact with each other" means not only (i) the case where the bonding material and the polymerization auxiliary material are brought into contact with each other so as to be laminated while forming their respective layers, but also (ii) the case where the bonding material and the polymerization auxiliary material are mixed with each other. In general, it is particularly preferred that the bonding material and the polymerization auxiliary material be brought into contact with each other so as to be laminated while forming their respective layers. In addition, when the bonding material and the polymerization auxiliary material are mixed, a composition containing no polymerizable monomer is used as the polymerization auxiliary material.

In this case, the contact step may be carried out in any mode as long as the bonding material and the polymerization auxiliary material can be brought into contact with each other, and for example, may be carried out by applying the bonding material onto an adherend, such as the first member, and then further applying the polymerization auxiliary material thereonto, or may be carried out by sufficiently mixing the bonding material and the polymerization auxiliary material before application onto the adherend, such as the first member. What mode is adopted for the contact step may be appropriately determined in consideration of, for example, the reactivity of the chemical polymerization initiator, the concentration of the first component contained in the bonding material and the concentration of the second component contained in the polymerization auxiliary material, the shape, size, applications, and the like of the adherend to be used in the bonding, and the curing time of the bonding material to be determined depending on the applications. When the bonding material and the polymerization auxiliary material are sufficiently mixed in the contact step, the bonding material-applying step is carried out by applying the mixture of the bonding material and the polymerization auxiliary material onto the surface of the first member, and the curing step is carried out by curing the mixture of the bonding material and the polymerization auxiliary material.

In addition, when bonding between the first member and the curable second member is performed, the polymerization auxiliary material may also have the function of the curable second member. As the polymerization auxiliary material having also the function of the curable second member, for example, a composition containing, in addition to the remainder constituent component of the chemical polymerization initiator for curing the bonding material, a polymerizable monomer, a polymerization initiator for curing the polymerization auxiliary material itself, and the like may be employed. In this case, when the bonding material and the polymerization auxiliary material having also the function of the curable second member are brought into contact with each other, the first member and the second member (cured matter of the polymerization auxiliary material having also the function of the curable second member) can be bonded through intermediation of the bonding material layer. In addition, when the third member is further used, the first member and the third member can be bonded through intermediation of the bonding material layer and a second member layer (layer formed by the curing of the polymerization auxiliary material having also the function of the curable second member). In this case, the bonded portion has a layered structure in which the first member, the bonding material layer, the second member layer, and the third member are laminated in the stated order.

In the contact step, in (i) the case where the bonding material and the polymerization auxiliary material are brought into contact with each other so as to be laminated while forming their respective layers, as long as the composition of the polymerization auxiliary material contains the remainder constituent component of the chemical polymerization initiator, the other components thereof are not particularly limited. Examples of the other components include a polymerizable monomer, a solvent, a filling material, a thermal polymerization initiator, a photopolymerization initiator, and a pigment. As those other components, known materials, including materials that may be employed in the bonding material according to this embodiment, may be appropriately employed. In addition, when the polymerization auxiliary material is employed also as the curable second member, the polymerization auxiliary material contains at least the remainder constituent component of the chemical polymerization initiator and a polymerizable monomer, and preferably further contains a filling material. In addition, in (ii) the case where the bonding material and the polymerization auxiliary material are mixed in the contact step, as described above, a composition containing no polymerizable monomer is used as the polymerization auxiliary material. Examples of such polymerization auxiliary material include: a composition containing the remainder constituent component (second component) of the chemical polymerization initiator and a volatile solvent; and a composition obtained by further adding a thickener, such as a binder resin, to the above-mentioned composition.

In addition, when the chemical polymerization initiator using a redox reaction is taken as an example of the chemical polymerization initiator, the bonding material and the polymerization auxiliary material may contain the oxidizing agent and the reducing agent, respectively, or vice versa. However, from the viewpoint that a higher bonding property is obtained, it is preferred that the bonding material contain the reducing agent and the polymerization auxiliary material contain the oxidizing agent. Although the cause of the higher bonding property has yet to be understood in detail, when the reducing agent is blended into the bonding material and the bonding material is applied onto the surface of the first member containing a polyaryletherketone resin, the reducing agent in the bonding material acts on the polyaryletherketone resin to reduce part of its carbonyl groups, and thus a carbon atom having two arylene groups, a hydroxyl group, and a hydrogen atom as substituents is generated on the surface of the first member. On such carbon atom having two arylene groups, a hydroxyl group, and a hydrogen atom as substituents, a radical easily occurs through hydrogen abstraction, and hence when the bonding material that has been brought into contact or mixed with the polymerization auxiliary material undergoes polymerization and curing, a bond is formed between the carbon atom adjacent to the hydroxyl group generated on the surface of the first member and (A) the polymerizable monomers that have been laminated. It is surmised that the bonding property is improved as a result of the foregoing.

In addition, as the reducing agent to be blended into the bonding material, in view of a balance among, for example, having high activity as the chemical polymerization initiator, keeping high fluidity to the extent possible immediately before the contact of the bonding material with the polymerization auxiliary material, and having storage stability, a fourth-period transition metal compound is preferably blended, and a +IV-valent vanadium compound is more preferred.

When the fourth-period transition metal compound is used for the bonding material and an amine compound is blended into the bonding material, the bonding strength-improving effect is slightly decreased as compared to the case where the amine compound is not blended. Accordingly, it is preferred that the amine compound be not blended into the bonding material. It is predicted that this is because the amine compound is coordinated to the transition metal in the fourth-period transition metal compound to decrease the activity of the fourth-period transition metal compound.

(C) Volatile Solvent

It is generally preferred that a volatile solvent be further blended into the bonding material according to this embodiment. The bonding material containing the volatile solvent has a lowered viscosity. Consequently, the bonding material easily penetrates fine unevenness on the surface of the first member containing a polyaryletherketone resin, and this is also advantageous for forming a uniform bonding material layer. In addition, (A) the polymerizable monomers migrate in the solvent to facilitate the migration of the hydrogen-bonding functional group in the p1h1 type polymerizable monomer to an appropriate position for forming an interaction with the polyaryletherketone resin, and hence the interaction between the polyaryletherketone resin and the bonding material layer can be further enhanced. The same applies to the case where the p2h1a1 type polymerizable monomer is further used in (A) the polymerizable monomers. That is, the volatile solvent can promote the migration of the aromatic ring in the p2h1a1 type polymerizable monomer to an appropriate position for forming an interaction with the polyaryletherketone resin.

In this case, the solvent is preferably removed from the system after playing the role of giving fluidity to a coating layer containing the bonding material. For this purpose, the solvent needs to be volatile. In the description of the present application, the "volatile solvent" refers to a solvent having a vapor pressure at 20° C. of 1.0 kPa or more. The volatile solvent is preferably sufficiently volatilized so as not to remain in and adversely affect the bonding material layer, and hence the vapor pressure at 20° C. is more preferably 2.0 kPa or more, still more preferably 5.0 kPa or more. Meanwhile, when the volatilization of the volatile solvent is excessively fast, the promoting effect on the migration of each of the hydrogen-bonding functional group in the p1h1 type polymerizable monomer, and the aromatic ring in the p2h1a1 type polymerizable monomer to be used as necessary to an appropriate position for forming an interaction with the polyaryletherketone resin is difficult to obtain. Accordingly, the vapor pressure of the volatile solvent at 20° C. is preferably 60 kPa or less, still more preferably 50 kPa or less. In addition, the boiling point of the volatile solvent is not particularly limited, but in view of the fact that a volatile solvent having a lower boiling point is easier to remove after the application of the bonding material onto the surface of the first member, the boiling point of the volatile solvent at 760 mmHg is preferably 100° C. or less, more preferably 80° C. or less.

In addition, the following effect is given as an effect of the use of the volatile solvent: in the application of the bonding material onto the surface of the first member, the application is further facilitated to allow easier handling.

The volatile solvent preferably has a ketone group. The use of the volatile solvent having a ketone group improves affinity between the first member and the bonding material, facilitates the penetration of the bonding material into fine unevenness on the surface of the first member, further enhances the interaction between the first member and the bonding material layer, and improves the bonding property.

The volatile solvent is preferably aprotic. When the volatile solvent is protic, an interaction between a proton donated from the volatile solvent and the carbonyl group of the polyaryletherketone resin inhibits the interaction between the hydrogen-bonding functional group in the p1h1 type polymerizable monomer contained in the bonding material and the carbonyl group of the polyaryletherketone resin. As a result, the interaction between the first member and the bonding material layer is further weakened, and the bonding property-improving effect may be limited.

Examples of the volatile solvent which are usable include aprotic solvents such as non-alcoholic solvents, e.g., acetone, methyl ethyl ketone, diethyl ketone, methyl n-propyl ketone, methyl isobutyl ketone, acetonitrile, tetrahydrofuran, diethyl ether, pentane, hexane, toluene, and ethyl acetate, and protic solvents such as alcoholic solvents, e.g., methanol, ethanol, 1-propanol, and isopropanol, and water.

Those volatile solvents may be used alone or a plurality of kinds thereof may be used as a mixture when the solvents can be homogeneously mixed. Of those volatile solvents, acetone, methyl ethyl ketone, diethyl ketone, methyl n-propyl ketone, and methyl isobutyl ketone are more preferred, and acetone is most preferred, in terms of, for example, being an aprotic solvent having a ketone group, and being biologically safe.

Such volatile solvent is removed by an air blow or the like after the application of the bonding material according to this embodiment onto the first member and before the curing of the bonding material.

The blending amount of the volatile solvent is not particularly limited, but is preferably appropriately selected within the range of from 10 parts by mass to 3,000 parts by mass with respect to 100 parts by mass of (A) the polymerizable monomers, depending on applications of the bonding material according to this embodiment. However, when the bonding material according to this embodiment is used in an application in which particularly low viscosity is not required, the blending amount of the volatile solvent falls within preferably the range of from 10 parts by mass to 500 parts by mass, preferably the range of from 20 parts by mass to 400 parts by mass, most preferably the range of from 50 parts by mass to 300 parts by mass with respect to 100 parts by mass of (A) the polymerizable monomers. When the blending amount of the volatile solvent is set to 10 parts by mass or more, the viscosity of the bonding material can be sufficiently lowered. Accordingly, it becomes easier to allow the bonding material to penetrate fine unevenness on the surface of the first member, and moreover, it also becomes easier to obtain the effect by which a uniform bonding material layer is formed. In addition, the effect by which the polymerizable monomers migrate in the solvent and migrate to an appropriate position for interacting with the polyaryletherketone resin material is also more easily obtained. In addition, when the blending amount of the volatile solvent is set to 500 parts by mass or less, the relative ratio of (A) the polymerizable monomers in the bonding material can be increased. As a result, when the bonding material is applied onto the surface of the first member, a sufficient amount of (A) the polymerizable monomers can be allowed to be present on the surface of the first member. Therefore, a uniform and firm bonding material layer can be more reliably formed, and a high bonding property can be more reliably obtained.

Together with the volatile solvent, a low-volatility solvent having a vapor pressure at 20° C. of less than 1.0 kPa may be blended into the bonding material. When the bonding material contains a large amount of the low-volatility solvent, the interaction between the polyaryletherketone resin contained in the first member and (A) the polymerizable monomers of the bonding material is inhibited or the polymerization and the curing of (A) the polymerizable monomers of the bonding material is inhibited, and thus the bonding property may be decreased. Accordingly, the low-volatility solvent is blended into the bonding material at preferably 10 mass % or less, more preferably 1 mass % or less, most preferably 0.1 mass % or less with respect to the blending amount of the volatile solvent.

(D) Coupling Agent

As necessary, a coupling agent having at least one or more first reactive groups each capable of reacting with an inorganic compound, and one or more second reactive groups each capable of reacting with an organic compound may be further blended into the bonding material according to this embodiment. The coupling agent is preferably used particularly when at least a portion of the first member in the vicinity of its adherend surface or the entirety of the first member is produced using a polyaryletherketone resin composite material containing a polyaryletherketone resin and an inorganic compound, such as an inorganic oxide. Details of the material composition of the first member suitable for bonding using the bonding material having blended thereinto the coupling agent are described later.

When the first member contains an inorganic compound, the bonding material containing the coupling agent can obtain a higher bonding property for the first member as compared to a bonding material containing no coupling agent.

As the coupling agent, a known one may be used without any limitation, and as a general example thereof, there is given a substance having a structure represented by the following general formula (I).

In the general formula (I): M represents an element selected from the group consisting of metal elements and metalloid elements; X represents each of the first reactive groups and represents a reactive group selected from the group consisting of (a) a hydroxyl group, and (b) a functional group capable of forming an M-OH structure in which a hydroxyl group is directly bonded to the element M by hydrolysis; Y represents each of the second reactive groups; Z represents a non-reactive functional group free of a reaction with any of the organic compound and the inorganic compound; and m represents an integer of 1 or more, n represents an integer of 1 or more, l represents an integer of 0 or 1 or more, and m+n+l is an integer equal to a valence of the element M.

Examples of the coupling agent include: a silane coupling agent in which the element M in the general formula (I) is silicon; a titanate-based coupling agent in which the element M is titanium; an aluminate-based coupling agent in which the element M is aluminum; and a zirconate-based coupling agent in which the element M is zirconium. Of those, a silane coupling agent is particularly suitable from the viewpoints of the bonding property and handleability.

The first reactive group X in the general formula (I) is: (a) a hydroxyl group (OH); or (b) a functional group capable of generating an M-OH structure in which a hydroxyl group (OH) is directly bonded to the element M by hydrolysis. Examples of the functional group shown in (b) may include an alkoxy group, an acryloxy group, a halogeno group, and an amino group. It is speculated that a bonding property is obtained through a reaction between the M-OH structure formed by the hydroxyl group shown in (a) or the M-OH structure to be generated by the hydrolysis of the functional group shown in (b), and the inorganic oxide in the polyaryletherketone resin composite material. From the viewpoint of its storage stability, the first reactive group X in the general formula (I) is preferably a functional group that has a small number of M-OH structures during storage, and that, for example, by being mixed with an acidic compound immediately before use to cause its hydrolysis to proceed, generates a large number of M-OH structures in each of which a hydroxyl group (OH) is directly bonded to the element M. Examples of such functional group include an alkoxy group and an acryloxy group. When hydroxyl groups are generated in a large amount during storage, there is a risk in that the bonding material cannot be stored for a long period of time owing to, for example, gelation of the bonding material through the occurrence of a condensation reaction between the hydroxyl groups. Accordingly, X preferably represents a functional group such as an alkoxy group or an acryloxy group. In terms of the ease of handling and the like, it is more preferred that X represent an alkoxy group having 1 to 5 carbon atoms, that is, the first reactive group X be OR where R represents an alkyl group having 1 to 5 carbon atoms. In particular, a methoxy group, an ethoxy group, or a propoxy group is still more preferred.

The second reactive group Y in the general formula (I) is a functional group containing a polymerizable functional group, and the functional group allows a bond to be formed between the coupling agent and (A) the polymerizable monomers contained in the bonding material to form a uniform and firm layer of the bonding material, to thereby improve the bonding property. The polymerizable functional group that the second reactive group Y has is preferably a radically polymerizable functional group in terms of low toxicity to a living body, high polymerization activity, and the like. Examples of the radically polymerizable functional group include functional groups such as a (meth)acryloyl group, a vinyl group, a styryl group, and an allyl group. Of those, a (meth)acryloyl group is particularly preferred in terms of polymerization rate and safety to a living body.

Z in the general formula (I) may represent any functional group as long as the functional group is a non-reactive functional group free of a reaction with any of the organic compound and the inorganic compound, and examples thereof include a hydrogen atom, an alkyl group, and an aryl group.

m, n, and l in the general formula (I) represent the numbers of functional groups X, Y, and Z, respectively. Accordingly, m+n+l is equal to the valence of the element M. In addition, the first reactive group X and the second reactive group Y are functional groups essential for further improving the bonding property for the first member containing a polyaryletherketone resin composite material, and hence m and n each independently represent an integer of 1 or more. Meanwhile, the functional group Z is not a functional group necessarily essential for obtaining the above-mentioned bonding property-improving effect, and hence l represents an integer of 0 or 1 or more. The first reactive group X is strongly related to the strength of the bonding between the polyaryletherketone resin composite material and the bonding material, and the second reactive group Y is strongly related to the strength of the layer of the bonding material. Accordingly, as the numbers represented by m and n increase, the interaction between the polyaryletherketone resin composite material and the bonding material is enhanced and a higher bonding property is obtained. Accordingly, l represents preferably 0 or 1, more preferably 0. In addition, the strength of the bonding between the polyaryletherketone resin composite material and the bonding material by the M-OH structure derived from the first reactive group X particularly strongly affects the bonding property, and hence m particularly preferably represents 2 or more. That is, for example, in the case of a silane coupling agent in which the element M is silicon having a valence of 4, a combination of m=3, n=1, and l=0, a combination of m=2, n=2, and l=0, or a combination of m=2, n=1, and l=1 is preferred, a combination of m=3, n=1, and l=0, or a combination of m=2, n=2, or l=0 is more preferred, and a combination of m=3, n=1, and l=0 is particularly preferred.

As the coupling agent, other than the compound represented by the general formula (I), a compound in which two or more compounds each represented by the general formula (I) are linked by a siloxane bond, or a compound in which two or more compounds each represented by the general formula (I) are linked via another functional group such as an alkylene group may also be used.

A suitable example of the coupling agent is one represented by the general formula (II).

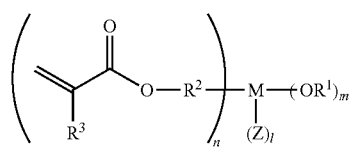

In the general formula (II), M represents, as in the case represented by the general formula (I), an element selected from the group consisting of metal elements and metalloid elements, $R^1$ represents an alkyl group having 1 to 5 carbon atoms, and $R^2$ represents any one of an alkylene group, an arylene group, an alkylenearylene group, and an arylenealkylene group. Those functional groups may each have any functional group as a side chain as long as the improving effect on the bonding property for the first member containing a polyaryletherketone resin composite material is not markedly inhibited, and examples thereof include a hydrogen atom, an alkyl group, a hydroxyl group, and an amino group. In addition, a functional group in which a plurality of the functional groups are linked via an ether bond, an ester bond, an amide bond, an amino group, or the like may be adopted. In addition, $R^3$ represents a hydrogen atom or a methyl group, and Z represents a hydrogen atom or an alkyl group having 1 to 5 carbon atoms. In addition, m, n, and l each represent the number of functional groups, m and n each independently represent an integer of 1 or more, and l represents an integer of 0 or 1 or more. m+n+l is equal to the valence of the element M. $R^1$ more preferably represents a methyl group or an ethyl group. $R^2$ more preferably represents an alkylene group having 1 to 15 carbon atoms in its main chain, or an arylene group, an alkylenearylene group, or an arylenealkylene group having 6 to 20 carbon atoms in its main chain. Z more preferably represents a hydrogen atom or a methyl group. l more preferably represents 0. The alkylenearylene group is such a group that in the general formula (II), an alkylene group moiety is bonded to the oxygen atom and an arylene group moiety is bonded to the element M, and the arylenealkylene group is such a group that an arylene group moiety is bonded to the oxygen atom and an alkylene group moiety is bonded to the element M. The same applies to the general formula (III) shown below.

As described above, the element M in the general formula (II) is preferably silicon, and such coupling agent may be represented by the following general formula (III).

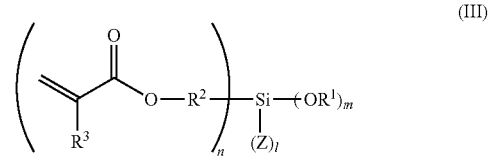

In the general formula (III), $R^1$ represents an alkyl group having 1 to 5 carbon atoms, and $R^2$ represents any one of an alkylene group, an arylene group, an alkylenearylene group, and an arylenealkylene group. Those functional groups may each have any functional group as a side chain as long as the improving effect on the bonding property for the first member containing a polyaryletherketone resin composite material is not markedly inhibited, and examples thereof include a hydrogen atom, an alkyl group, a hydroxyl group, and an amino group. In addition, a functional group in which a plurality of the functional groups are linked via an ether bond, an ester bond, an amide bond, an amino group, or the like may be adopted. In addition, $R^3$ represents a hydrogen atom or a methyl group, and Z represents a hydrogen atom or an alkyl group having 1 to 5 carbon atoms. In addition, m, n, and l each represent the number of functional groups, m and n each independently represent an integer of 1 or more, and l represents an integer of 0 or 1 or more. m+n+l=4. $R^1$ more preferably represents a methyl group, an ethyl group, or a propyl group. R² more preferably represents an alkylene group having 1 to 15 carbon atoms in its main chain, or an arylene group, an alkylenearylene group, or an arylenealkylene group having 6 to 20 carbon atoms in its main chain. Z more preferably represents a hydrogen atom or a methyl group. m, n, and l satisfy preferably a combination of m=3, n=1, and l=0, a combination of m=2, n=2, and l=0, or a combination of m=2, n=1, and l=1, more preferably a combination of m=3, n=1, l=0.

Examples of the coupling agent which is suitably used include silane coupling agents, such as γ-methacryloyloxypropyltrimethoxysilane, γ-methacryloyloxypropyltriethoxysilane, γ-methacryloyloxypropyltriisopropylsilane, γ-methacryloxypropylmethyldimethoxysilane, γ-methacryloyloxypropyltris(methoxyethoxy)silane, γ-methacryloxypropylmethyldiethoxysilane, ω-methacryloyloxydecyltrimethoxysilane, (methacryloxymethyl)methyldimethoxysilane, (methacryloxymethyl)methyldiethoxysilane, methacryloxymethyltrimethoxysilane, O-(methacryloyloxyethyl)-N-(triethoxysilylpropyl)carbamate, N-(3-methacryloyl-2-hydroxypropyl)-3-aminopropyltriethoxysilane, 3-(n-methacryloyloxyphenyl)propyltrimethoxysilane, γ-methacryloyloxypropyltriisopropoxysilane, and 3-(3-methoxy-4-methacryloyloxyphenyl)propyltrimethoxysilane.

One kind of the coupling agents may be used alone, or two or more kinds thereof may be used in combination.

The blending amount of the coupling agent is not particularly limited, but falls within preferably the range of from 1 part by mass to 30 parts by mass, more preferably the range of from 2 parts by mass to 20 parts by mass, still more preferably the range of from 3 parts by mass to 10 parts by mass with respect to 100 parts by mass of the total amount of the coupling agent and (A) the polymerizable monomers. When the blending amount of the coupling agent is set to fall within the range of from 1 part by mass to 30 parts by mass, the bonding property for the first member containing a polyaryletherketone resin composite material can be further improved. A reason for this is that when the blending amount of the coupling agent is set to 1 part by mass or more, sufficient bonding is easily formed between the inorganic compound present on the surface of the first member and the coupling agent. Another reason is that when the blending amount of the coupling agent is set to 30 parts by mass or less, the formation of a brittle layer resulting from dehydration condensation between M-OH structures of the excess coupling agent in the vicinity of the inorganic compound present on the surface of the first member can be suppressed.

When the coupling agent in which the first reactive group X in the general formula (I) is a functional group capable of generating an M-OH structure in which a hydroxyl group (OH) is directly bonded to the element M by hydrolysis is used, it is also preferred that a p1h1 type polymerizable monomer having an acidic group in the molecule be used in (A) the polymerizable monomers. The use of the p1h1 type polymerizable monomer having an acidic group in the molecule can promote the hydrolysis reaction of the coupling agent to efficiently generate the M-OH structure. As a result, the reaction between the bonding material and the inorganic compound contained in the polyaryletherketone resin composite material proceeds more to improve the bonding property.

When the p1h1 type polymerizable monomer having an acidic group in the molecule is blended into the bonding material, the p1h1 type polymerizable monomer having an acidic group in the molecule and the coupling agent may be stored in the same package. However, from the viewpoint of storage stability, it is preferred that a bonding material component containing the coupling agent and a bonding material component containing the p1h1 type polymerizable monomer having an acidic group in the molecule be stored in separate packages. This is because when the coupling agent and the p1h1 type polymerizable monomer having an acidic group in the molecule are stored in a mixed state, the hydrolysis reaction of the functional group capable of generating an M-OH structure in which a hydroxyl group (OH) is directly bonded to the element M by hydrolysis proceeds during the storage. In this case, the advantage of the functional group, i.e., high storage stability is difficult to obtain.

In the case of using the coupling agent, the blending amount of the p1h1 type polymerizable monomer having an acidic group in the molecule is preferably from 1 part by mass to 40 parts by mass, more preferably from 5 parts by mass to 20 parts by mass with respect to 100 parts by mass of all the polymerizable monomers. When the blending amount of the p1h1 type polymerizable monomer having an acidic group in the molecule is set to 1 mass % or more, the hydrolysis of the first reactive group X (functional group capable of generating an M-OH structure by hydrolysis) in the coupling agent can be sufficiently promoted, and a high bonding property can be more reliably obtained. In addition, when the blending amount of the p1h1 type polymerizable monomer having an acidic group in the molecule is set to 40 parts by mass or less, an increase in water-absorbing property of the bonding material in excess of what is needed can be suppressed. Therefore, even when the bonding material is used in a moist environment (e.g., in an oral cavity), the bonding material layer is not easily deteriorated owing to excessive water absorption, and hence, in particular, a decrease in long-term bonding property can be more reliably suppressed.

In addition, the p1h1 type polymerizable monomer is used as an essential component of the bonding material according to this embodiment. Accordingly, in the case of further using the coupling agent represented by any one of the general formulae (I) to (III), when the first reactive group X of the coupling agent is a hydroxyl group, it is surmised that the following effect is exhibited: the M-OH structure containing the hydroxyl group interacts with the hydrogen-bonding functional group of the p1h1 type polymerizable monomer to improve the binding strength of the bonding material layer. In addition, when the first reactive group X of the coupling agent is a functional group capable of forming an M-OH structure by hydrolysis, it is surmised that the following effect is exhibited: the M-OH structure generated by the hydrolysis of the functional group interacts with the hydrogen-bonding functional group of the p1h1 type polymerizable monomer to improve the binding strength of the bonding material layer. That is, a higher bonding property is expected to be obtained by virtue of such action.

(E) Other Components

The bonding material according to this embodiment may contain a filling material as necessary. The filling material is not particularly limited, and, for example, a known inorganic filling material, organic filling material, or organic-inorganic composite filling material may be employed. The incorporation of the filling material increases the strength of the bonding material that has penetrated fine unevenness present on the surface of the first member to further enhance the interaction between the first member and the bonding material layer, with the result that a high bonding property is easily obtained.

Examples of the inorganic filling material include quartz, silica, silica-alumina, silica-titania, silica-zirconia, lantanum glass, barium glass, strontium glass, and fluoroaluminosilicate glass. When any such inorganic filling material is used, one treated with a silane coupling agent is preferred. Examples of the silane coupling agent include methyltrimethoxysilane, methyltriethoxysilane, methyltrichlorosilane, dimethyldichlorosilane, trimethylchlorosilane, hexamethyldisilazane, vinyltrimethoxysilane, vinyltriethoxysilane, vinyltrichlorosilane, vinyltriacetoxysilane, vinyltris(β-methoxyethoxy)silane, γ-methacryloyloxypropyltrimethoxysilane, γ-methacroyloxypropyltris(β-methoxyethoxy)silane, γ-chloropropyltrimethoxysilane, γ-chloropropylmethyldimethoxysilane, γ-glycidoxypropyltrimethoxysilane, γ-glycidoxypropylmethyldiethoxysilane, β-(3,4-epoxycyclohexyl)ethyltrimethoxysilane, N-phenyl-γ-aminopropyltrimethoxysilane, 11-methacryloyloxyundecyltrimethoxysilane, and 11-methacryloyloxyundecylmethyldimethoxysilane.

Examples of the organic filling material include particles formed of organic polymers, such as polymethyl methacrylate, a polymethyl methacrylate-polyethyl methacrylate copolymer, an ethylene-vinyl acetate copolymer, a styrene-butadiene copolymer, an acrylonitrile-styrene copolymer, and an acrylonitrile-butadiene-styrene copolymer.

An example of the organic-inorganic composite filling material is a particulate organic-inorganic composite filling material obtained by mixing the above-mentioned inorganic particles and a polymerizable monomer, followed by polymerization and pulverization.

Meanwhile, when the bonding material contains a large amount of the filling material, the viscosity of the bonding material tends to increase to decrease the bonding property. Besides, the interaction between the hydrogen-bonding functional group of the p1h1 type polymerizable monomer contained in the bonding material and the carbonyl group of the polyaryletherketone resin becomes difficult to obtain, with the result that the bonding property is decreased in some cases. The same applies to the case where the bonding material further contains the p2h1a1 type polymerizable monomer. This is because the interaction between the aromatic ring of the p2h1a1 type polymerizable monomer and the aromatic ring of the polyaryletherketone resin becomes difficult to obtain. Accordingly, the amount of the filling material to be added to the bonding material is preferably 400 parts by mass or less, more preferably 100 parts by mass or less, more preferably 50 parts by mass or less, more preferably 20 parts by mass or less, more preferably 10 parts by mass or less with respect to 100 parts by mass of (A) the polymerizable monomers.

The particle diameter and shape of the filling material are not particularly limited, but from the viewpoint of forming a uniform bonding material layer, the particle diameter is preferably small. As the particle diameter of the filling material, the average primary particle diameter of 100 randomly selected particles measured with a transmission electron microscope is preferably 100 μm or less, more preferably from 0.01 μm to 10 μm, still more preferably from 0.01 μm to 1 μm.

In addition, as necessary, the bonding material may contain components other than the components (A) to (D), such as a polymerization inhibitor, a polymerization retarder, a dye, a pigment, and a perfume.

<Physical Properties of Bonding Material and Production Method Therefor>

When bonding is performed through the use of the bonding material according to this embodiment, it is important for obtaining a high bonding property that the bonding material penetrate fine unevenness present on the surface of the first member containing a polyaryletherketone resin. In addition, it is also important for obtaining a high bonding property that a functional group of the polyaryletherketone resin and a functional group of (A) the polymerizable monomers of the bonding material interact with each other. Accordingly, it is more preferred that the bonding material have low viscosity when applied onto the surface of the first member. When the viscosity of the bonding material is low, the bonding material easily penetrates fine unevenness present on the surface of the first member.

In addition, from the viewpoints of improving the application property of the bonding material for the first member and facilitating handling at the time of bonding, the viscosity of the bonding material at 23° C. falls within preferably the range of from 0.3 cP to 3,000 cP, more preferably the range of from 0.4 cP to 500 cP, still more preferably the range of from 0.5 cP to 30 cP, most preferably the range of from 0.5 cP to 10 cP. The viscosity of the bonding material may be adjusted by further blending a volatile solvent into the bonding material. The viscosity may be measured in a thermostatic chamber kept at 23° C. with a cone-plate viscometer under red light for preventing a change in viscosity due to polymerization during measurement.

A production method for the bonding material according to this embodiment is not particularly limited, and the bonding material may be produced in accordance with a known production method for a bonding material. In general, all the components to be blended only need to be weighed out and thoroughly mixed until becoming homogeneous.

<Bonding Method, First Member, Second Member, and Third Member>

As long as the bonding material according to this embodiment is used at least for bonding onto the first member containing a polyaryletherketone resin, the bonding method using the bonding material according to this embodiment is not particularly limited. In addition, in bonding, another composition, such as the polymerization auxiliary material, may be used in combination. In addition, when the bonding material contains a volatile solvent, before curing of the coating layer of the bonding material formed on the surface of the first member, the volatile solvent in the coating layer may be removed by air drying, an air blow, or the like.

In addition, the bonding material according to this embodiment is more preferably used for a first member having a roughened adherend surface. The first member having a roughened adherend surface has increased surface unevenness, and hence when the bonding material according to this embodiment is applied onto such adherend surface, a higher bonding property can be obtained. Treatment for roughening the adherend surface only needs to be carried out before the application of the bonding material according to this embodiment onto the first member. A method for the roughening treatment is not particularly limited, and a known roughening treatment method may be employed. From the viewpoints of simplicity and safety, sandblast treatment is preferred. The sandblast treatment may be generally carried out by spraying alumina particles each having a particle diameter of from several μm to several hundreds of μm onto the adherend surface of the first member at a pressure of from several tens of kPa to several MPa through the use of a sandblast apparatus.

A procedure for bonding may be appropriately determined depending on, for example, the kinds of the bonding object and the polymerization initiator contained in the bonding material. When only the first member is used as the bonding object, for example, it is appropriate that the bonding material be applied onto the surface of the first member, followed by curing of the bonding material. When a thermal polymerization initiator or a photopolymerization initiator is used as the polymerization initiator, the bonding material may be cured by heating or photoirradiation after being applied. In addition, when a chemical polymerization initiator is used as the polymerization initiator, a mixture obtained in advance by mixing the bonding material and the polymerization auxiliary material may be applied onto the surface of the first member, or the bonding material and the polymerization auxiliary material may be separately applied onto the surface of the first member to bring the bonding material and the polymerization auxiliary material into contact with each other on the surface of the first member. In this case, the curing of the bonding material is initiated at the time when the bonding material and the polymerization auxiliary material are brought into contact with each other.

When the first member and the solid state second member are used as the bonding object, for example, the following procedure may be performed: the bonding material is applied onto the surface of at least one member out of the first member and the solid state second member, and then the first member and the solid state second member are brought into contact with each other through intermediation of the coating layer of the bonding material, followed by curing of the bonding material. When the polymerization auxiliary material is used, bonding may be performed by applying a mixture obtained by mixing the bonding material and the polymerization auxiliary material onto the surface of at least one of the first member or the solid state second member, and then attaching the first member and the solid state second member onto each other through intermediation of a coating layer formed of the mixture. Alternatively, bonding may be performed by applying the bonding material onto the surface of one of the members, applying the polymerization auxiliary material onto the surface of the other member, and then attaching the first member and the solid state second member onto each other.

When the first member and the curable second member are used as the bonding object, for example, one-step curing treatment of simultaneously curing the bonding material and the curable second member may be carried out after applying the bonding material onto the surface of the first member and then further applying the curable second member, or two-step curing treatment involving sequentially applying and curing the bonding material, and then sequentially applying and curing the curable second member may be carried out. The timing, number of times, and curing method (heat curing, photocuring, or chemical curing) of the curing treatment may be appropriately selected depending on the kinds of the polymerization initiators to be blended into the bonding material and the curable second member.

When the bonding material contains part of the components of a chemical polymerization initiator, the curable second member (polymerization auxiliary material) contains at least the remainder component of the chemical polymerization initiator (for curing the bonding material), a polymerization initiator (all components) for curing the curable second member (polymerization auxiliary material), and a polymerizable monomer, and preferably further contains a filling material. When the polymerization initiator for curing the curable second member (polymerization auxiliary material) is a chemical polymerization initiator, the remainder component of the chemical polymerization initiator (for curing the bonding material) preferably doubles as part of the components of the chemical polymerization initiator for curing the curable second member (polymerization auxiliary material).

In addition, when the bonding material contains no chemical polymerization initiator and contains at least any one polymerization initiator out of a thermal polymerization initiator and a photopolymerization initiator, the curable second member contains at least a polymerization initiator (all components) and a polymerizable monomer, and preferably further contains a filling material.

In addition, when the third member is further used, for example, the following procedure may be performed: the bonding material is applied onto the surface of the first member, the curable second member is applied onto the surface of the third member, and then the surface of the first member having applied thereonto the bonding material is brought into contact with the surface of the third member having applied thereonto the curable second member, followed by curing of the bonding material and the curable second member. In this case, the following procedure may also be performed: any one member out of the bonding material and the curable second member is first cured before contact between the first member and the third member, and the other member is cured after contact between the first member and the third member.

In addition, the following procedure may be performed: the bonding material and the curable second member are applied in the stated order onto the surface of the first member, and then the surface of the first member having applied thereonto the bonding material and the curable second member is brought into contact with the third member, followed by curing of the bonding material and the curable second member. In this case, the following procedure may be performed: the bonding material is applied onto the surface of the first member and cured, then the curable second member is further applied, and the surface of the first member having applied thereonto the curable second member is brought into contact with the third member, followed by curing of the curable second member. Alternatively, the following procedure may be performed: the curable second member and the bonding material are applied in the stated order onto the surface of the third member, and then the surface of the third member having applied thereonto the curable second member and the bonding material is brought into contact with the first member, followed by curing of the curable second member and the bonding material. In this case, the following procedure may be performed: the curable second member is applied onto the surface of the third member and cured, then the bonding material is further applied, and the surface of the third member having applied thereonto the bonding material is brought into contact with the first member, followed by curing of the bonding material. The member onto which each of the bonding material and the curable second member is to be applied, the timing of the application, and the timing of the curing of each of those members may be appropriately selected.

The first member to be employed in the bonding method according to this embodiment is not particularly limited as long as the member contains a polyaryletherketone resin. However, it is necessary that a material for forming at least a portion of the first member in the vicinity of its adherend surface (adherend portion-forming material) contain a polyaryletherketone resin, and the adherend portion-forming material contains the polyaryletherketone resin at preferably 20 mass % or more, more preferably 30 mass % or more. When the adherend portion-forming material contains the polyaryletherketone resin at 20 mass % or more, the interaction between the hydrogen-bonding functional group of the p1h1 type polymerizable monomer contained in the bonding material and the ketone group of the polyaryletherketone resin can be further enhanced, and hence a higher bonding property is easily obtained. Further, when the bonding material contains the p2h1a1 type polymerizable monomer, the interaction between the aromatic ring of the p2h1a1 type polymerizable monomer and the aromatic ring of the polyaryletherketone resin based on stack formation can be further enhanced, and hence an even higher bonding property can be obtained. Besides, the strength of the adherend portion-forming material can be further increased.

The first member may have its entirety formed of the adherend portion-forming material, or may have a part including a portion in the vicinity of its adherend surface formed of the adherend portion-forming material and have the other parts formed of a material different from the adherend portion-forming material. In addition, the adherend portion-forming material may be formed only of the polyaryletherketone resin, or may be a mixture of the polyaryletherketone resin and any other material. Examples of the other material include another resin than the polyaryletherketone resin, and a filling material, and other examples include various additives to be used as trace components, such as a pigment and a stabilizer.

The polyaryletherketone resin is a thermoplastic resin containing at least an aromatic group, an ether group (ether bond), and a ketone group (ketone bond) as structural units thereof, and often has a linear polymer structure having phenylene groups bonded via an ether group and a ketone group. Typical examples of the polyaryletherketone resin include polyetherketone (PEK), polyetheretherketone (PEEK), polyetherketoneketone (PEKK), and polyetherketoneetherketoneketone (PEKEKK). The aromatic group contained in the structural unit of the polyaryletherketone resin may have a structure having two or more benzene rings like a biphenyl structure. In addition, the structural unit of the polyaryletherketone resin may contain a sulfonyl group or another monomer unit that is copolymerizable.

The other resin that may be blended with the polyaryletherketone resin is not particularly limited, but is preferably a resin that does not significantly degrade the physical properties of the polyaryletherketone resin, such as rigidity and toughness. Examples thereof include a polyarylate resin, a polycarbonate resin, a polyethylene terephthalate resin, a polyphthalamide resin, a polytetrafluoroethylene resin, and a polyphenylene ether resin. When the polyaryletherketone resin and the other resin are blended, the blending ratio of the polyaryletherketone resin in the resin blend is preferably 50 mass % or more, more preferably 70 mass % or more, still more preferably 90 mass % or more, still more preferably 99 mass % or more.

As the filling material that may be blended into the polyaryletherketone resin, a known one may be employed without any particular limitation, but an inorganic filling material (inorganic compound) is suitable. As the inorganic compound, any of inorganic oxides, such as silica, and non-oxide-based inorganic compounds, such as SiC and SiN, may be used. Of those, an inorganic oxide is preferably used. Examples of materials for the inorganic oxide include: silica glass, borosilicate glass, soda glass, aluminosilicate glass, and fluoroaluminosilicate glass, and glass containing a heavy metal (e.g., barium, strontium, or zirconium); glass ceramics, such as crystallized glass obtained by depositing a crystal in any such glass, and a crystallized glass obtained by depositing a crystal such as diopside or leucite; composite inorganic oxides, such as silica-zirconia, silica-titania, and silica-alumina; oxides produced by adding Group I inorganic oxides to those composite oxides; and inorganic oxides, such as silica, alumina, titania, and zirconia. One kind of those inorganic compounds may be used alone, or two or more kinds thereof may be used in combination.

Also in the case where the adherend portion-forming material is formed of a polyaryletherketone resin composite material containing an inorganic compound and a polyaryletherketone resin, for the same reason as that in the above-mentioned case, the polyaryletherketone resin composite material contains the polyaryletherketone resin at preferably 20 mass % or more, preferably 30 mass % or more.

In addition, the polyaryletherketone resin composite material contains the inorganic compound at preferably 15 mass % or more, preferably 25 mass % or more. In addition, the blending ratio of the inorganic compound in the polyaryletherketone resin composite material is preferably 70 mass % or less, more preferably 50 mass % or less.

Examples of such polyaryletherketone resin composite material include: a) a composite material obtained by mixing only the polyaryletherketone resin and the inorganic compound; b) a composite material obtained by mixing a resin matrix formed of a mixture of the polyaryletherketone resin and another resin with the inorganic compound; and c) a composite material obtained by further adding, to the composite material shown in a) or b), a trace component such as a pigment or a stabilizer.

In addition, the polyaryletherketone resin composite material containing 20 mass % or more of the polyaryletherketone resin and 15 mass % or more of the inorganic compound has the following features: a) being able to easily obtain high mechanical strength as compared to the polyaryletherketone resin alone, any other resin alone, or a mixture of the polyaryletherketone resin and the other resin; b) being strong against brittle fracture as compared to a material formed only of the inorganic compound; and c) being excellent in water resistance and corrosion resistance as compared to general metal materials except for some expensive metal materials excellent in corrosion resistance, such as gold and platinum. As described above, for bonding onto the first member using such polyaryletherketone resin composite material at least as the adherend portion-forming material, a bonding material containing a coupling agent is suitably used.

From the viewpoint of mechanical strength, the blending ratio of the inorganic compound in the polyaryletherketone resin composite material is preferably high. However, when the blending ratio is excessively high, the polyaryletherketone resin composite material may be difficult to produce. In addition, in the matrix of the polyaryletherketone resin composite material, separation between the inorganic compound and the polyaryletherketone resin becomes liable to occur. Accordingly, in the case of the bonding material using a coupling agent, the bonding property-improving effect of the formation of bonding between the coupling agent and the inorganic compound is difficult to obtain. However, such problem becomes easier to avoid when the blending ratio of the inorganic compound in the polyaryletherketone resin composite material is set to 70 mass % or less.

As the inorganic compound to be used for the polyaryletherketone resin composite material, the above-mentioned inorganic compounds may be appropriately employed. Of those, an inorganic oxide, such as silica, alumina, titania, zirconia, silica-zirconia, silica-titania, or silica-alumina, is preferably used, and a silicon-containing inorganic oxide, such as silica, silica-zirconia, silica-titania, or silica-alumina, is more preferably used. In particular, when the bonding material containing a coupling agent is used, the silicon-containing inorganic oxide can provide a higher bonding property by virtue of its high reactivity with the coupling agent (in particular, a silane coupling agent).

In addition, the solid state second member is not particularly limited as long as the member is formed of a known solid material, but is preferably a member containing a polyaryletherketone resin like the first member. In terms of material composition and structure of the member, the first member and the solid state second member may be identical to or different from each other. When the solid state second member is formed of a member containing a polyaryletherketone resin like the first member, the bonding material according to this embodiment can also be bonded onto the solid state second member with a high bonding property as in the case of bonding onto the first member. A material for forming the solid state second member may be, for example, any of: a) artificially produced or purified materials, such as various resins including a polyaryletherketone resin, materials each containing, as a main component, organic matter other than a resin (e.g., a pulp material), metals, and inorganic compounds similar to those usable in the first member; b) a composite material using two or more kinds of the materials shown in a); or c) non-artificial biological materials, such as teeth and bones. Further, as with the first member, the solid state second member may have its entirety formed of its adherend portion-forming material, or may have a part including a portion in the vicinity of its adherend surface formed of the adherend portion-forming material and have the other parts formed of a material different from the adherend portion-forming material.

In addition, as described above, the composition of the curable second member contains at least a polymerization initiator and a polymerizable monomer, and preferably further contains a filling material. When the polymerization initiator to be used for curing the curable second member is a chemical polymerization initiator, the curable second member is generally formed of a first material containing part of the components of the chemical polymerization initiator, and a second material containing the remainder component of the chemical polymerization initiator, and the first material and the second material are mixed at the time of use. As the constituent components of the curable second member, materials that may be used in the bonding material according to this embodiment may be employed in appropriate combination. For the composition of the curable second member, composition different from that of the bonding material according to this embodiment to be actually used for bonding is generally selected. The curable second member contains a polymerizable monomer, and hence the curable second member and the bonding material according to this embodiment are firmly bonded. In addition, when the third member is further used, the polymerizable monomer contained in the curable second member interacts with the surface of the third member as well, to thereby allow the curable second member and the third member to be bonded. For the composition of the curable second member, composition having high affinity for the adherend portion-forming material of the third member is preferably selected. In addition, when the curable second member is used, for bonding, the bonding material according to this embodiment and the curable second member need to be brought into contact with each other in a mode in which the bonding material and the curable second member are laminated so as to form layers without being mixed.

The third member is not particularly limited as long as the member is formed of a known solid material, and a member similar to the solid state second member may be used. However, as the third member, in general, a member whose adherend portion-forming material does not contain a polyaryletherketone resin is preferably used.

<Bonding in Field of Dentistry>

The bonding method according to this embodiment, and the bonding material and bonding kit to be used in the bonding method may be used in any applications. In addition, as the bonding object, at least a first member appropriate for the applications is used, and as necessary, a) the solid state second member, b) the curable second member, or c) the curable second member and the third member are further used. However, the bonding method according to this embodiment, and the bonding material and bonding kit to be used in the bonding method are preferably used in the field of dentistry.

In this case, as a first member that may be used as a dental member (dental first member), there are given, for example, a denture, an artificial tooth, a denture base, a dental implant, a dental crown/bridge restoration material, and an abutment construction material each of which is partially or entirely produced using a polyaryletherketone resin. In addition, as a curable second member that may be used as a dental member (dental curable second member), there are given, for example, a dental composite resin, dental cement, a dental hard resin, a dental bonding material, and a dental autopolymerizing resin. Further, as the third member, there are given, for example, a natural tooth, a dental metal material, a dental resin-based material, and a dental ceramic material.

A bonding mode to be carried out in dental treatment is appropriately selected depending on the purpose of the treatment, and typical examples thereof include bonding modes exemplified below:

(A) a bonding mode involving applying the bonding material according to this embodiment onto the surface of the dental first member, and further applying the dental curable second member, followed by simultaneous curing of the bonding material according to this embodiment and the dental curable second member;

(B) a bonding mode involving applying the bonding material according to this embodiment onto the surface of the dental first member, followed by curing of the bonding material, and further applying the dental curable second member, followed by curing of the dental curable second member; and (C) a bonding mode involving applying the dental curable second member onto the surface of the third member, then applying the bonding material according to this embodiment, and finally simultaneously curing the dental curable second member and the bonding material according to this embodiment under a state in which the first member is in contact with the portion having applied thereto the bonding material.

When the polymerization initiator contained in the bonding material is a photopolymerization initiator, a thermal polymerization initiator, or a chemical polymerization initiator (all components), bonding may be performed in any one of the bonding modes (A) to (C). In addition, when the polymerization initiator contained in the bonding material is part of the components of a chemical polymerization initiator, bonding may be performed in the bonding mode (A) or (C).

In each of the bonding mode (A) and the bonding mode (B), when, for example, a photopolymerization initiator is used as each of the polymerization initiators to be used for the bonding material and the dental curable second member, curing treatment is carried out by performing photoirradiation. In this case, the dental curable second member is used as, for example, a so-called dental composite resin to be used for restoration of a defective portion in a tooth or the like, and contains at least a polymerizable monomer, the photopolymerization initiator, and a filling material. In addition, an example of the dental first member is an artificial tooth produced using a material containing a polyaryletherketone resin. In addition, in the bonding mode (A), when a chemical polymerization initiator is used as each of the polymerization initiators to be used for the bonding material and the dental curable second member, the curing of the bonding material is initiated by contact between the bonding material and the dental curable second member (polymerization auxiliary material). The curing of the dental curable second member is initiated by the chemical polymerization initiator contained in the dental curable second member (for curing the dental curable second member). In this case, the dental curable second member is, for example, used as dental cement, and contains at least a polymerizable monomer, the chemical polymerization initiator, and a filling material. In addition, an example of the dental first member is an artificial tooth produced using a material containing a polyaryletherketone resin.

In the bonding mode (C), when, for example, a chemical polymerization initiator is used as the polymerization initiator to be used for the bonding material and the dental curable second member, curing treatment is initiated by contact between the bonding material and the dental curable second member. In this case, the bonding material according to this embodiment is used as a dental primer having a self-bonding property. In addition, the dental curable second member functions also as the polymerization auxiliary material for the bonding material, and for example, may be used as so-called dental cement. The dental cement contains at least a polymerizable monomer, the remainder component of the chemical polymerization initiator for curing the bonding material, the polymerization initiator to be blended for the purpose of curing the dental cement itself, and a filling material. In addition, an example of the first member may be a dental crown/bridge restoration member produced using a material containing a polyaryletherketone resin, and an example of the third member is a natural tooth having a defective portion.

A dental member is required to have, as characteristics for withstanding use in an oral cavity, mechanical strength for withstanding the pressure to be repeatedly applied at the time of occlusion, and water resistance against saliva. In this regard, such need is sufficiently met with extreme ease by the dental first member containing a polyaryletherketone resin having excellent mechanical strength and chemical durability.

From the viewpoints of a color tone and physical properties, as the polyaryletherketone resin to be used as a dental material, in particular, a dental restoration material, it is preferred to use polyetheretherketone having a repeating unit in which ether groups and ketone groups constituting its main chain are arranged in the order "ether-ether-ketone", or polyetherketoneketone having a repeating unit in which the groups are arranged in the order "ether-ketone-ketone". In addition, of those, as the dental first member to be used in the bonding method according to this embodiment, polyetherketoneketone having a large number of ketone groups each capable of interacting with the hydrogen-bonding functional group of the p1h1 type polymerizable monomer contained in the bonding material is more preferred. In this case, the ratio of the polyetherketoneketone in all the polyaryletherketone resins to be used for the dental first member is more preferably 50 mass % or more.

In addition, from the viewpoint that higher mechanical strength is obtained, as the material for forming the dental first member, the above-mentioned polyaryletherketone resin composite material is preferably used. Further, in consideration of the ease with which a color tone similar to that of a natural tooth is obtained, safety, and the like in use in an oral cavity over a long period of time, as the inorganic compound to be used for the polyaryletherketone resin composite material, an inorganic oxide, such as silica, alumina, titania, zirconia, silica-zirconia, silica-titania, or silica-alumina, is preferably used, and a silicon-containing inorganic oxide, such as silica, silica-zirconia, silica-titania, or silica-alumina, is more preferably used. In addition, the entirety of the dental first member is preferably formed of the polyaryletherketone resin, and the entirety of the member is more preferably formed of the polyaryletherketone resin composite material.

When the dental first member and another dental member are bonded onto each other, it is necessary that a high bonding property be obtained as in bonding between members to be used in other fields. However, under unique circumstances in bonding in the field of dentistry unlike bonding in any other field, it is more desirable that the following characteristics be further satisfied as much as possible:

(a) a high bonding property can be maintained over a long period of time even in a moist oral cavity (high bonding durability);
(b) bonding work in a small oral cavity is simple and easy (excellent operability);
(c) a bonding material can be stored over a long period of time without causing degeneration in order for the bonding material to be used in an extremely small amount each time dental treatment is performed (excellent storage stability).

However, in the bonding method according to this embodiment, when the p1h1 type polymerizable monomer containing a mercapto group as the hydrogen-bonding functional group is used in (A) the polymerizable monomers to be used for the bonding material, higher bonding durability can be obtained, and when the polymerizable monomer capable of generating a mercapto group in the molecule by tautomerism is used in (A) the polymerizable monomers to be used for the bonding material, all of high bonding durability, excellent operability, and excellent storage stability can be simultaneously achieved. In addition, when the dental first member containing a polyaryletherketone resin composite material is used in bonding, through the use of the bonding material containing the coupling agent having the first reactive group X formed of a functional group capable of generating an M-OH structure by hydrolysis, excellent storage stability can be obtained.

In addition, when the dental first member, such as a dental crown/bridge restoration member, and the dental third member, such as a natural tooth, are bonded using a dental bonding material and a dental curable second member (dental cement) that are commercially available at present, for example, problems as described below are liable to occur.

(i) The dental first member is bonded in a state of floating or being out of position with respect to the dental third member. Accordingly, after the bonding, machining work for the dental first member is required, resulting in increases in burden on dentists and patients.

(ii) A cured layer of the dental bonding material to be formed between the dental first member and the dental third member has an increased thickness. This results in poor appearance and degraded aesthetics.

However, when the dental first member and the dental third member are bonded using the bonding material according to this embodiment including part of the constituent components of the chemical polymerization initiator and the dental cement containing the remainder constituent component of the chemical polymerization initiator (polymerization auxiliary material doubling as the curable second member), the above-mentioned problems can be suppressed. The reason for this is as described below. In this case, it takes some time for the bonding material to sufficiently cure after contact between the bonding material and the dental cement. Accordingly, through pressure contact between the dental first member and the dental third member during bonding, the bonding material layer having fluidity before complete curing can be thinned.

<Bonding Kit>

The bonding kit according to this embodiment only needs to include at least the bonding material according to this embodiment and the first member. In this case, the bonding kit may include a plurality of the first members, and the plurality of the first members may be identical to or different from each other in shape and size. In addition, the bonding kit may include the solid state second member and/or the curable second member. In addition, when the bonding kit includes the curable second member, the bonding kit may further include the third member. In this case, the numbers, shapes, and sizes of the second members and the third members to be included in the bonding kit are not particularly limited. In addition, when the bonding material included in the bonding kit contains part of the components of a chemical polymerization initiator serving as the polymerization initiator, the bonding kit also includes the polymerization auxiliary material.

EXAMPLES

The present invention is specifically described below by way of Examples. However, the present invention is not limited thereto. Abbreviations and names shown in Examples are as described below.

[Polymerizable Monomer Having Two or More Polymerizable Functional Groups in Molecule]
(Polymerizable Monomer Having Hydrogen-Bonding Functional Group and Aromatic Ring in Molecule)
bisGMA: 2,2-bis[4-(3-methacryloyloxy)-2-hydroxypropoxyphenyl]propane
(Polymerizable Monomer Having Hydrogen-Bonding Functional Group and not Having Aromatic Ring in Molecule)
UDMA: 1,6-bis(methacrylethyloxycarbonylamino)-2,2,4-trimethylhexane
PM2: bis(2-methacryloyloxyethyl) hydrogen phosphate
PM2 also has an acidic group containing, in a part thereof, a hydroxyl group serving as a hydrogen-bonding functional group.
(Polymerizable Monomer not Having Hydrogen-Bonding Functional Group and Aromatic Ring in Molecule)
3G: triethylene glycol dimethacrylate
[Polymerizable Monomer Having One Polymerizable Functional Group in Molecule]
(Polymerizable Monomer Having Hydrogen-Bonding Functional Group in Molecule)
PM1: 2-methacryloyloxyethyl dihydrogen phosphate
PM1 also has an acidic group containing, in a part thereof, a hydroxyl group serving as a hydrogen-bonding functional group.

HEMA: 2-hydroxyethyl methacrylate
MTU-6: See the following chemical formula.
MMT-11: See the following chemical formula.
VTD: See the following chemical formula.
5VS: See the following chemical formula.
MTU-6, MMT-11, VTD, and 5VS are each a polymerizable monomer capable of generating a mercapto group in the molecule by tautomerism.

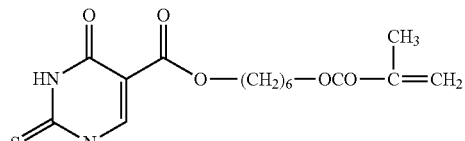

MTU-6

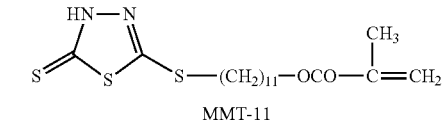

MMT-11

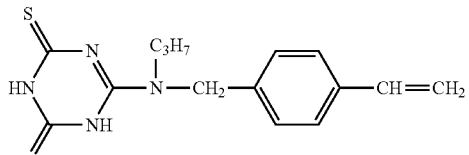

VTD

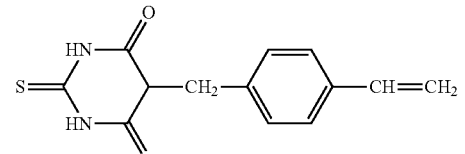

5VS (Polymerizable Monomer not Having Hydrogen-Bonding Functional Group in Molecule)
MMA: methyl methacrylate
  [Coupling Agent]
(Silane Coupling Agent)
MPS: γ-methacryloyloxypropyltrimethoxysilane
MDS: ω-methacryloyloxydecyltrimethoxysilane
MBS: 3-(3-methoxy-4-methacryloyloxy phenyl)propyltrimethoxysilane
  [Polymerization Initiator]
<Photopolymerization Initiator>
(α-Diketone)
CQ: camphorquinone
(Amine Compound)
DMBE: ethyl p-dimethylaminobenzoate
  <Chemical Polymerization Initiator>
(Organic Peroxide)
BPO: benzoyl peroxide
(Tertiary Amine)
DEPT: N,N-diethanol-p-toluidine
(+IV-Valent Vanadium Compound)
BMOV: bis(maltolato)oxovanadium(IV)
  [Volatile Solvent]
IPA: isopropyl alcohol

[Filling Material]

F1: silica having an average primary particle diameter of 18 nm and having a surface treated with methyltrichlorosilane F2: spherical silica-zirconia (average particle diameter: 0.4 μm) having a surface treated with γ-methacryloyloxypropyltrimethoxysilane F3: irregular shape silica-zirconia (average particle diameter: 3 μm) having a surface treated with γ-methacryloyloxypropyltrimethoxysilane (Production of Adherend (First Member))

<Production of First Member C1>

As a material for forming an adherend (first member), there was used a composite material (polyaryletherketone resin composite material) obtained by mixing a polyetheretherketone resin (manufactured by Daicel-Evonik Ltd.: VESTAKEEP M2G) and spherical silica (volume average particle diameter: 1.0 μm) having a surface treated with γ-methacryloyloxypropyltrimethoxysilane, which served as a filling material (inorganic oxide), at 39 parts by volume of the filling material with respect to 100 parts by volume of the polyetheretherketone resin. The content of the polyetheretherketone resin in the composite material is 60.3 mass %, and the balance is the inorganic oxide. Those materials were mixed by the following procedure. First, predetermined amounts of the polyetheretherketone resin and the inorganic oxide were measured out, and loaded into a kneader LABO PLASTOMILL (manufactured by Toyo Seiki Seisaku-sho, Ltd.). Then, those materials were melt-kneaded for 5 minutes under the conditions of a test temperature of 370° C. and a number of rotations of 100 rpm. Further, a melt-kneaded product obtained by the melt-kneading was molded with a heat press machine into a plate shape having a thickness of about 2 mm. Thus, a first member C1 was obtained.

<Production of First Member C2>

As a material for forming an adherend (first member), there was used a composite material (polyaryletherketone resin composite material) obtained by mixing a polyetheretherketone resin (manufactured by Daicel-Evonik Ltd.: VESTAKEEP M2G) and spherical silica (volume average particle diameter: 1.0 μm) having a surface treated with γ-methacryloyloxypropyltrimethoxysilane, which served as a filling material (inorganic oxide), at 15 parts by volume of the filling material with respect to 100 parts by volume of the polyetheretherketone resin. The content of the polyetheretherketone resin in the composite material is 79.8 mass %, and the balance is the inorganic oxide. Those materials were mixed by the following procedure. First, predetermined amounts of the polyetheretherketone resin and the inorganic oxide were measured out, and loaded into a kneader LABO PLASTOMILL (manufactured by Toyo Seiki Seisaku-sho, Ltd.). Then, those materials were melt-kneaded for 5 minutes under the conditions of a test temperature of 370° C. and a number of rotations of 100 rpm. Further, a melt-kneaded product obtained by the melt-kneading was molded with a heat press machine into a plate shape having a thickness of about 2 mm. Thus, a first member C2 was obtained.

<Production of First Member C3>

A polyetheretherketone resin (manufactured by Daicel-Evonik Ltd.: VESTAKEEP M2G) was molded with a heat press machine into a plate shape having a thickness of about 2 mm. Thus, a first member C3 was obtained.

Test methods are as described below.

(Initial Tensile Bonding Strength Measurement)

The adherend surface of a first member was polished with #800 waterproof abrasive paper, and then sandblast treatment (a sandblast apparatus was used to spray alumina particles each having a particle diameter of about 50 μm at a pressure of about 0.2 MPa for 10 seconds) was performed to roughen the adherend surface of the first member. After that, the first member having its adherend surface roughened was washed by being exposed to ultrasound for 5 minutes in water, and then exposed to ultrasound for 5 minutes in acetone. Then, a double sided tape having a hole having a diameter of 3 mm was attached onto the adherend surface.

Then, a prepared bonding material was applied to the hole. The resultant was left to stand for 60 seconds, and then compressed air was caused to blow thereon for about 10 seconds, followed by drying. As necessary, the bonding material was subjected to photoirradiation with a dental irradiation device (TOKUSO POWER LITE, manufactured by Tokuyama Dental Corporation; optical output density: 700 mW/cm$^2$) for 10 seconds to be cured. Dental cement (BISTITE II, manufactured by Tokuyama Dental Corporation) was applied as a curable second member onto the cured bonding material, and an attachment made of stainless steel was further pressure-bonded onto the dental cement to produce a bonded test piece. The photoirradiation using the dental irradiation device was carried out only in the case where the bonding material contained a photopolymerization initiator. In addition, when the bonding material contained, as a polymerization initiator, part of the constituent components of a chemical polymerization initiator, BISTITE II or a separately produced curable second member was used as a curable second member doubling as a polymerization auxiliary material for the bonding material.

The above-mentioned bonded test piece was kept at 37° C. for 24 hours, and then subjected to a tensile test using a tensile tester (Autograph, manufactured by Shimadzu Corporation) at a cross-head speed of 2 mm/min to measure initial tensile bonding strength between the first member and the bonding material. The initial tensile bonding strength between the first member and the bonding material was measured for each of four test pieces of each of the bonding materials of Examples or Comparative Examples, and an average value and a standard deviation (S.D.) were determined.

(Durable Tensile Bonding Strength Measurement)

The adherend surface of a first member was polished with #800 waterproof abrasive paper, and then roughening was performed by sandblast treatment (a sandblast apparatus was used to spray alumina particles each having a particle diameter of about 50 μm at a pressure of about 0.2 MPa for 10 seconds). After that, the first member having its adherend surface roughened was washed by being exposed to ultrasound for 5 minutes in water, and then exposed to ultrasound for 5 minutes in acetone. Then, a double sided tape having a hole having a diameter of 3 mm was attached onto the adherend surface.

Then, a prepared bonding material was applied to the hole. The resultant was left to stand still for 10 seconds, and then compressed air was caused to blow thereon for about 10 seconds, followed by drying. As necessary, the bonding material was subjected to photoirradiation with a dental irradiation device (TOKUSO POWER LITE, manufactured by Tokuyama Dental Corporation; optical output density: 700 mW/cm$^2$) for 10 seconds to be cured. Dental cement (BISTITE II, manufactured by Tokuyama Dental Corporation) was applied as a curable second member onto the cured bonding material, and an attachment made of stainless steel was further pressure-bonded onto the dental cement to produce a bonded test piece. The photoirradiation using the dental irradiation device was carried out only in the case where the bonding material contained a photopolymerization initiator. In addition, when the bonding material contained, as a polymerization initiator, part of the constituent components of a chemical polymerization initiator, BISTITE II or a separately produced curable second member was used as a curable second member doubling as a polymerization auxiliary material for the bonding material.

The above-mentioned bonded test piece was kept at 37° C. for 24 hours, and then put into a thermal shock tester. The following operation was repeated 3,000 times: the test piece was immersed in a water bath at 4° C. for 1 minute, then transferred to a water bath at 60° C. and immersed therein for 1 minute, and returned again to the water bath at 4° C. Then, the bonded test piece was subjected to a tensile test using a tensile tester (Autograph, manufactured by Shimadzu Corporation) at a cross-head speed of 2 mm/min to measure durable tensile bonding strength between the first member and the bonding material. The durable tensile bonding strength between the first member and the bonding material was measured for each of five test pieces of Examples or Comparative Examples, and an average value and a standard deviation (S.D.) were determined.

(Bonding Durability)

Bonding durability was determined on the basis of the following equation. Average values determined by the above-mentioned two kinds of tensile bonding strength measurement were used as values for "durable tensile bonding strength" and "initial tensile bonding strength" in the equation.

Bonding durability [%]=Durable tensile bonding strength/Initial tensile bonding strength×100

(Bonding Material Layer Thickness)

The adherend surface of a first member was polished with #800 waterproof abrasive paper, and then sandblast treatment (a sandblast apparatus was used to spray alumina particles each having a particle diameter of about 50 µm at a pressure of about 0.2 MPa for 10 seconds) was performed to roughen the adherend surface of the first member. After that, the first member having its adherend surface roughened was washed by being exposed to ultrasound for 5 minutes in water, and then exposed to ultrasound for 5 minutes in acetone.

Then, a bonding material was applied onto the adherend surface. The resultant was left to stand still for 10 seconds, and then compressed air was caused to blow thereon for about 10 seconds, followed by drying. As necessary, the bonding material was subjected to photoirradiation with a dental irradiation device (TOKUSO POWER LITE, manufactured by Tokuyama Dental Corporation; optical output density: 700 mW/cm$^2$) for 10 seconds to be cured. Dental cement (BISTITE II, manufactured by Tokuyama Dental Corporation) was applied as a curable second member onto the cured bonding material, and an attachment produced by curing a dental hard resin (manufactured by Tokuyama Dental Corporation: PEARLESTE) was further pressure-bonded onto the dental cement to produce a test piece. The photoirradiation using the dental irradiation device was carried out only in the case where the bonding material contained a photopolymerization initiator. In addition, when the bonding material contained, as a polymerization initiator, part of the constituent components of a chemical polymerization initiator, BISTITE II or a separately produced curable second member was used as a curable second member doubling as a polymerization auxiliary material for the bonding material. In addition, the amount of the bonding material per unit area to be applied onto the adherend surface was set to be substantially the same in each of Examples and Comparative Examples.

The above-mentioned test piece was kept at 37° C. for 24 hours, and then the test piece was cut with a diamond cutter perpendicularly to the adherend surface to expose a cross-section of the bonded site. The cross-section of the bonded site was polished with #3000 waterproof abrasive paper, and then the thickness of the layer of the bonding material was measured as a bonding material layer thickness with a laser microscope (manufactured by Keyence Corporation).

Example 1

50 g of bisGMA and 50 g of 3G, which served as (A) the polymerizable monomers, 2 g of CQ and 2 g of DMBE, which served as (B) the polymerization initiator, and 100 g of acetone, which served as (C) the volatile solvent, were added, and mixed by stirring to provide a bonding material according to Example 1. The composition of the bonding material is shown in Table 1. With the use of the first member C1 as an adherend, the bonding material was used to measure initial tensile bonding strength, durable tensile bonding strength, and a bonding material layer thickness. The bonding material was subjected to photoirradiation before the tests. The results are shown in Table 4.

Example 2

20 g of bisGMA and 80 g of 3G, which served as (A) the polymerizable monomers, 2 g of CQ and 2 g of DMBE, which served as (B) the polymerization initiator, and 100 g of acetone, which served as (C) the volatile solvent, were added, and mixed by stirring to provide a bonding material according to Example 2. The composition of the bonding material is shown in Table 1. With the use of the first member C1 as an adherend, the bonding material was used to measure initial tensile bonding strength. The bonding material was subjected to photoirradiation before the tests. The results are shown in Table 4.

Examples 3 to 14 and 16 to 18, and Comparative Examples 1 to 5

Bonding materials were obtained in accordance with Example 2 except that the composition was changed as shown in Table 1 and Table 3, and initial tensile bonding strength was measured. The compositions of the bonding materials are shown in Table 1 and Table 3. The evaluation results are shown in Table 4.

Example 15

50 g of bisGMA and 50 g of 3G, which served as (A) the polymerizable monomers, 2 g of CQ and 2 g of DMBE, which served as (B) the polymerization initiator, 100 g of acetone, which served as (C) the volatile solvent, and 70 g of F1, which served as the filling material component, were added, and mixed by stirring to provide a bonding material according to Example 15. The composition of the bonding material is shown in Table 1. With the use of the first member C1 as an adherend, the bonding material was used to measure initial tensile bonding strength. The bonding material was subjected to photoirradiation before the tests. The results are shown in Table 4.

Example 19

50 g of bisGMA and 50 g of 3G, which served as (A) the polymerizable monomers, 0.1 g of BMOV, which served as part of the constituent components of (Bc) the chemical polymerization initiator serving as (B) the polymerization initiator, and 100 g of acetone, which served as (C) the volatile solvent, were added, and mixed by stirring to provide a bonding material according to Example 19. The composition of the bonding material is shown in Table 2. With the use of the first member C1 as an adherend, the bonding material was used to measure initial tensile bonding strength and a bonding material layer thickness. The bonding material was not subjected to photoirradiation before the tests.

In addition, as the curable second member (polymerization auxiliary material), there were used 4 g of D-2.6E (2,2-bis(4-methacryloyloxypolyethoxyphenyl)propane), 1 g of bisGMA, 3 g of 3G, 1 g of PM1, and 1 g of PM2, which served as polymerizable monomer components, 0.3 g of DEPT, which served as a chemical polymerization initiator component for curing the curable second member, BPO, which served as a chemical polymerization initiator component for curing the curable second member and as the remainder component of (Bc) the chemical polymerization initiator to be used for curing of a bonding material, and 17.5 g of F2 and 12.5 g of F3, which served as filling material components. The adjustment and use of the curable second member were carried out by the following procedure. First, the components except for BPO were mixed in the above-mentioned blending amounts to produce a paste. Next, immediately before the measurement tests, 8.7 mg of BPO was added and mixed with respect to 1 g of the paste to produce the curable second member, which was used for the measurement tests. The results are shown in Table 4.

Example 20

50 g of bisGMA and 50 g of 3G, which served as (A) the polymerizable monomers, 0.1 g of BMOV, which served as part of the constituent components of (Bc) the chemical polymerization initiator serving as (B) the polymerization initiator, and 100 g of acetone, which served as (C) the volatile solvent, were added, and mixed by stirring to provide a bonding material according to Example 20. The composition of the bonding material is shown in Table 2. With the use of the first member C1 as an adherend, the bonding material was used to measure initial tensile bonding strength and a bonding material layer thickness. The bonding material was not subjected to photoirradiation before the tests. In addition, BISTITE II was used as the curable second member (polymerization auxiliary material). The BISTITE II contains BPO as the remainder constituent component of (Bc) the chemical polymerization initiator.

Example 21

50 g of bisGMA and 50 g of 3G, which served as (A) the polymerizable monomers, 0.1 g of BPO, which served as part of the constituent components of (Bc) the chemical polymerization initiator serving as (B) the polymerization initiator, and 100 g of acetone, which served as (C) the volatile solvent, were added, and mixed by stirring to provide a bonding material according to Example 21. The composition of the bonding material is shown in Table 2. With the use of the first member C1 as an adherend, the bonding material was used to measure initial tensile bonding strength and a bonding material layer thickness. The bonding material was not subjected to photoirradiation before the tests.

In addition, as the curable second member (polymerization auxiliary material), there were used 4 g of D-2.6E, 1 g of bisGMA, 3 g of 3G, 1 g of PM1, and 1 g of PM2, which served as polymerizable monomer components, 0.3 g of DEPT, which served as a chemical polymerization initiator component for curing the curable second member and as the remainder component of (Bc) the chemical polymerization initiator to be used for curing of a bonding material, BPO, which served as a chemical polymerization initiator component for curing the curable second member, and 17.5 g of F2 and 12.5 g of F3, which served as filling material components. The adjustment and use of the curable second member were carried out by the following procedure. First, the components except for BPO were mixed in the above-mentioned blending amounts to produce a paste. Next, immediately before the measurement tests, 8.7 mg of BPO was added and mixed with respect to 1 g of the paste to produce the curable second member, which was used for the measurement tests. The results are shown in Table 4.

Example 22

50 g of bisGMA and 50 g of 3G, which served as (A) the polymerizable monomers, 0.1 g of DEPT, which served as part of the constituent components of (Bc) the chemical polymerization initiator serving as (B) the polymerization initiator, and 100 g of acetone, which served as (C) the volatile solvent, were added, and mixed by stirring to provide a bonding material according to Example 22. The composition of the bonding material is shown in Table 2. With the use of the first member C1 as an adherend, the bonding material was used to measure initial tensile bonding strength and a bonding material layer thickness. The bonding material was not subjected to photoirradiation before the tests.

In addition, as the curable second member (polymerization auxiliary material), there were used 4 g of D-2.6E, 1 g of bisGMA, 3 g of 3G, 1 g of PM1, and 1 g of PM2, which served as polymerizable monomer components, 0.3 g of DEPT, which served as a chemical polymerization initiator component for curing the curable second member, BPO, which served as a chemical polymerization initiator component for curing the curable second member and as the remainder component of (Bc) the chemical polymerization initiator to be used for curing of a bonding material, and 17.5 g of F2 and 12.5 g of F3, which served as filling material components. The adjustment and use of the curable second member were carried out by the following procedure. First, the components except for BPO were mixed in the above-mentioned blending amounts to produce a paste. Next, immediately before the measurement tests, 8.7 mg of BPO was added and mixed with respect to 1 g of the paste to produce the curable second member, which was used for the measurement tests. The results are shown in Table 4.

Example 23

30 g of bisGMA, 20 g of 3G, 15 g of PM1, and 15 g of PM2, which served as (A) the polymerizable monomers, 0.1 g of BMOV, which served as part of the constituent components of (Bc) the chemical polymerization initiator serving as (B) the polymerization initiator, and 100 g of acetone, which served as (C) the volatile solvent, were added, and mixed by stirring to provide a bonding material according to Example 23. The composition of the bonding material is shown in Table 2. With the use of the first member C1 as an adherend, the bonding material was used to measure initial tensile bonding strength and a bonding material layer thickness. The bonding material was not subjected to photoirradiation before the tests.

In addition, as the curable second member (polymerization auxiliary material), there were used 4 g of D-2.6E, 1 g of bisGMA, 3 g of 3G, 1 g of PM1, and 1 g of PM2, which served as polymerizable monomer components, 0.3 g of DEPT, which served as a chemical polymerization initiator component for curing the curable second member, BPO, which served as a chemical polymerization initiator component for curing the curable second member and as the remainder component of (Bc) the chemical polymerization initiator to be used for curing of a bonding material, and 17.5 g of F2 and 12.5 g of F3, which served as filling material components. The adjustment and use of the curable second member were carried out by the following procedure. First, the components except for BPO were mixed in the above-mentioned blending amounts to produce a paste. Next, immediately before the measurement tests, 8.7 mg of BPO was added and mixed with respect to 1 g of the paste to produce the curable second member, which was used for the measurement tests. The results are shown in Table 4.

Example 24

20 g of bisGMA, 20 g of 3G, 8 g of PM1, and 8 g of PM2, which served as (A) the polymerizable monomers, 1 g of CQ and 1 g of DMBE, which served as (B) the polymerization initiator, and 50 g of acetone which served as (C) the volatile solvent, were added, and mixed by stirring to provide a composition A. 20 g of bisGMA, 20 g of 3G, and 4 g of MPS, which served as (A) the polymerizable monomers, 1 g of CQ and 1 g of DMBE, which served as (B) the polymerization initiator, and 50 g of acetone, which served as (C) the volatile solvent, were added, and mixed by stirring to provide a composition B. Equal amounts of the composition A and the composition B were taken and mixed to provide a bonding material according to Example 24, which was quickly used for the tests. The composition of the bonding material is shown in Table 3. With the use of the first member C1 as an adherend, the bonding material was used to measure initial tensile bonding strength. The bonding material was subjected to photoirradiation before the tests. The results are shown in Table 4.

Examples 25 and 26

Bonding materials were obtained in accordance with Example 24 except that the composition was changed as shown in Table 3, and initial tensile bonding strength was measured. The compositions of the bonding materials are shown in Table 3. The evaluation results are shown in Table 4.

Example 27

49.95 g of bisGMA, 49.95 g of 3G, and 0.1 g of MTU-6, which served as (A) the polymerizable monomers, 2 g of CQ and 2 g of DMBE, which served as (B) the polymerization initiator, and 100 g of acetone, which served as (C) the volatile solvent, were added, and mixed by stirring to provide a bonding material according to Example 27. The composition of the bonding material is shown in Table 3. With the use of the first member C1 as an adherend, the bonding material was used to measure initial tensile bonding strength and durable tensile bonding strength. The bonding material was subjected to photoirradiation before the tests. The results are shown in Table 4.

Examples 28 to 30

Bonding materials were obtained in accordance with Example 27 except that the composition was changed as shown in Table 3, and initial tensile bonding strength and durable tensile bonding strength were measured. The compositions of the bonding materials are shown in Table 3. The evaluation results are shown in Table 4.

Example 31

19.9875 g of bisGMA, 19.9875 g of 3G, 8 g of PM1, 8 g of PM2, and 0.05 g of MTU-6, which served as (A) the polymerizable monomers, 1 g of CQ and 1 g of DMBE, which served as (B) the polymerization initiator, and 50 g of acetone, which served as (C) the volatile solvent, were added, and mixed by stirring to provide a composition A. 19.9875 g of bisGMA, 19.9875 g of 3G, 4 g of MPS, and 0.05 g of MTU-6, which served as (A) the polymerizable monomers, 1 g of CQ and 1 g of DMBE, which served as (B) the polymerization initiator, 50 g of acetone, which served as (C) the volatile solvent, were added, and mixed by stirring to provide a composition B. Equal amounts of the composition A and the composition B were taken and mixed to provide a bonding material according to Example 31, which was quickly used for the tests. The composition of the bonding material is shown in Table 3. With the use of the first member C1 as an adherend, the bonding material was used to measure initial tensile bonding strength and durable tensile bonding strength. The bonding material was subjected to photoirradiation before the tests. The results are shown in Table 4.

Example 32

Initial tensile bonding strength and durable tensile bonding strength were measured by using the same bonding material and the same technique as those of Example 27 except that the first member C2 was used as an adherend.

Example 33

Initial tensile bonding strength and durable tensile bonding strength were measured by using the same bonding material and the same technique as those of Example 27 except that the first member C3 was used as an adherend.

TABLE 1

| | Content of each type of polymerizable monomer in all polymerizable monomers (mass %) | | | | Bonding material composition [part(s) by mass] | | | | | | | | | | | | |
|---|---|---|---|---|---|---|---|---|---|---|---|---|---|---|---|---|---|
| | | | | | Polymerizable monomer | | | | | | | | | | | | |
| Number of polymerizable functional groups | 2 or more | 1 or more | 2 or more | 2 or more | 2 | | | | 1 | | | | | | | | |
| Hydrogen-bonding functional group | | Present | Present | Present | Present | Present | Present (*1) | Absent | Present (*1) | Present | Absent | | | | | | |
| Aromatic ring | | | | Present | Present | Absent | Absent | Absent | | | | Polymerization initiator | | Volatile solvent | | Filling material | Kind of first member |
| Type/abbreviation | p2 type | p1h1 type | p2h1 type | p2h1a1 type | bisGMA | UDMA | PM2 | 3G | PM1 | HEMA | MMA | CQ | DMBE | Acetone | IPA | F1 | |
| Example 1 | 100.0 | 50.0 | 50.0 | 50.0 | 50 | | 50 | | | | | 2 | 2 | 100 | | | C1 |
| Example 2 | 100.0 | 20.0 | 20.0 | 20.0 | 20 | | 80 | | | | | 2 | 2 | 100 | | | C1 |
| Example 3 | 60.0 | 100.0 | 60.0 | 0.0 | | 60 | | | 40 | | | 2 | 2 | 100 | | | C1 |
| Example 4 | 60.0 | 60.0 | 60.0 | 0.0 | | 60 | | | | | 40 | 2 | 2 | 100 | | | C1 |
| Example 5 | 60.0 | 60.0 | 20.0 | 0.0 | | 20 | 40 | | 40 | | | 2 | 2 | 100 | | | C1 |
| Example 6 | 100.0 | 80.0 | 80.0 | 0.0 | | 80 | 20 | | | | | 2 | 2 | 100 | | | C1 |
| Example 7 | 50.0 | 50.0 | 0.0 | 0.0 | | | | 50 | | 50 | | 2 | 2 | 100 | | | C1 |
| Example 8 | 65.0 | 80.0 | 45.0 | 30.0 | 30 | | 15 | 20 | 15 | 20 | | 2 | 2 | 100 | | | C1 |
| Example 9 | 70.0 | 80.0 | 50.0 | 20.0 | 20 | 15 | 15 | 20 | 15 | 15 | | 2 | 2 | 100 | | | C1 |
| Example 10 | 50.0 | 50.0 | 0.0 | 0.0 | | | | 50 | | 50 | | 2 | 2 | 500 | | | C1 |
| Example 11 | 50.0 | 50.0 | 0.0 | 0.0 | | | | 50 | | 50 | | 2 | 2 | 300 | | | C1 |
| Example 12 | 50.0 | 50.0 | 0.0 | 0.0 | | | | 50 | | 50 | | 2 | 2 | 50 | | | C1 |
| Example 13 | 50.0 | 50.0 | 0.0 | 0.0 | | | | 50 | | 50 | | 2 | 2 | 10 | | | C1 |
| Example 14 | 100.0 | 50.0 | 50.0 | 50.0 | 50 | | 50 | | | | | 2 | 2 | | 100 | | C1 |
| Example 15 | 100.0 | 50.0 | 50.0 | 50.0 | 50 | | 50 | | | | | 2 | 2 | 100 | | 7 | C1 |
| Example 16 | 100.0 | 50.0 | 50.0 | 50.0 | 50 | | 50 | | | | | 2 | 2 | | | | C1 |
| Example 17 | 90.0 | 10.0 | 0.0 | 0.0 | | | | 90 | | 10 | | 2 | 2 | 100 | | | C1 |
| Example 18 | 70.0 | 30.0 | 0.0 | 0.0 | | | | 70 | | 30 | | 2 | 2 | 100 | | | C1 |

*1: A hydrogen-bonding functional group constitutes part of an acidic group as well.

TABLE 2

| | Content of each type of polymerizable monomer in all polymerizable monomers (mass %) | | | | Bonding material composition [part(s) by mass] | |
|---|---|---|---|---|---|---|
| | | | | | Polymerizable monomer | |
| Number of polymerizable functional groups | 2 or more | 1 or more | 2 or more | 2 or more | 2 | 1 |

TABLE 2-continued

| | Type/abbreviation | p2 type | p1h1 type | p2h1 type | p2h1a1 type | bisGMA | UDMA | PM2 | 3G | PM1 | HEMA |
|---|---|---|---|---|---|---|---|---|---|---|---|
| Hydrogen-bonding functional group | | Present | Present | Present | Present | Present | Present | Present (*1) | Absent | Present (*1) | Present |
| Aromatic ring | | | | | Present | Present | Absent | Absent | Absent | | |
| Example 19 | | 100.0 | 50.0 | 50.0 | 50.0 | 50 | | | 50 | | |
| Example 20 | | 100.0 | 50.0 | 50.0 | 50.0 | 50 | | | 50 | | |
| Example 21 | | 100.0 | 50.0 | 50.0 | 50.0 | 50 | | | 50 | | |
| Example 22 | | 100.0 | 50.0 | 50.0 | 50.0 | 50 | | | 50 | | |
| Example 23 | | 65.0 | 80.0 | 45.0 | 30.0 | 30 | | 15 | 20 | 15 | 20 |

| | Bonding material composition [part(s) by mass] | | | | | | | | |
|---|---|---|---|---|---|---|---|---|---|
| | Polymerizable monomer 1 | | | | | | Volatile solvent | Filling material F1 | Kind of first member |
| Number of polymerizable functional groups | 1 | | | | | | | | |
| Hydrogen-bonding functional group | Absent | | | | | | | | |
| Aromatic ring | | | | | | | | | |
| Type/abbreviation | MMA | \multicolumn{5}{c}{Polymerization initiator} | | | | |
| | | CQ | DMBE | BMOV | BPO | DEPT | Acetone | IPA | |
| Example 19 | | | | 0.1 | | | 100 | | C1 |
| Example 20 | | | | 0.1 | | | 100 | | C1 |
| Example 21 | | | | | 0.1 | | 100 | | C1 |
| Example 22 | | | | | | 0.1 | 100 | | C1 |
| Example 23 | | | | 0.1 | | | 100 | | C1 |

*1: A hydrogen-bonding functional group constitutes part of an acidic group as well.

TABLE 3

| | Content of each type of polymerizable monomer in all polymerizable monomers (mass %) | | | | | Bonding material composition [part(s) by mass] | | | | | | | | | | | | | | | | | | | |
|---|---|---|---|---|---|---|---|---|---|---|---|---|---|---|---|---|---|---|---|---|---|---|---|---|---|
| | Number of polymerizable functional groups | | Hydrogen-bonding functional groups | Aromatic ring | | Polymerizable monomer | | | | | | | | | | | Coupling agent | | | Polymerization initiator | | Volatile solvent | | Filling material | Kind of first |
| Type/ abbreviation | 2 or more | 1 or more | 2 or more | 2 or more | p2 type | p1h1 type | p2h1 type | p2h1a1 type | bisGMA Pre-sent | UDMA Ab-sent | PM2 Pre-sent (*1) | 3G Ab-sent | PM1 Pre-sent (*1) | HEMA Pre-sent | MTU-6 Pre-sent (*2) | MMT-11 Pre-sent (*2) | VTD Pre-sent (*2) | 5VS Pre-sent (*2) | MMA Ab-sent | MPS | MDS | MBS | CQ | DMBE | Acetone | IPA | F1 | member |
| Example 24 | 91.7 | 58.3 | 50.0 | 41.7 | 40 | | 8 | 40 | | 8 | | | | | | | 4 | | | 2 | 2 | 100 | | | C1 |
| Example 25 | 91.7 | 58.3 | 50.0 | 41.7 | 40 | | 8 | 40 | | 8 | | | | | | | | 4 | | 2 | 2 | 100 | | | C1 |
| Example 26 | 91.7 | 58.3 | 50.0 | 41.7 | 40 | | 8 | 40 | | 8 | | | | | | | | | 4 | 2 | 2 | 100 | | | C1 |
| Example 27 | 99.9 | 50.1 | 50.0 | 50.0 | 49.95 | | | 49.95 | | | 0.1 | | | | | | | | | 2 | 2 | 100 | | | C1 |
| Example 28 | 99.9 | 50.1 | 50.0 | 50.0 | 49.95 | | | 49.95 | | | | 0.1 | | | | | | | | 2 | 2 | 100 | | | C1 |
| Example 29 | 99.9 | 50.1 | 50.0 | 50.0 | 49.95 | | | 49.95 | | | | | 0.1 | | | | | | | 2 | 2 | 100 | | | C1 |
| Example 30 | 99.9 | 50.1 | 50.0 | 50.0 | 49.95 | | | 49.95 | | | | | | 0.1 | | | | | | 2 | 2 | 100 | | | C1 |
| Example 31 | 91.6 | 58.4 | 49.9 | 41.6 | 39.975 | | 8 | 39.975 | | 8 | 0.1 | | | | | | | | | 2 | 2 | 100 | | | C1 |
| Example 32 | 99.9 | 50.1 | 50.0 | 50.0 | 49.95 | | | 49.95 | | | 0.1 | | | | | | | | | 2 | 2 | 100 | | | C2 |
| Example 33 | 99.9 | 50.1 | 50.0 | 50.0 | 49.95 | | | 49.95 | | | 0.1 | | | | | | | | | 2 | 2 | 100 | | | C3 |
| Comparative Example 1 | 30.0 | 90.0 | 20.0 | 20.0 | 20 | | | 10 | | | | | | 70 | | | | | | 2 | 2 | 100 | | | C1 |
| Comparative Example 2 | 30.0 | 30.0 | 30.0 | 0.0 | | 30 | | | 30 | | | | 40 | | | | | | 70 | 2 | 2 | 100 | | | C1 |
| Comparative Example 3 | 30.0 | 100.0 | 30.0 | 0.0 | | | | | 10 | 20 | | | | 30 | | | 4 | | | 2 | 2 | 100 | | | C1 |
| Comparative Example 4 | 50.0 | 0.0 | 0.0 | 0.0 | | | | 50 | 50 | | | | | | | | | | 50 | 2 | 2 | 100 | | | C1 |
| Comparative Example 5 | 100.0 | 50.0 | 50.0 | 50.0 | 50 | 50 | | 50 | | | | | | | | | | | | 2 | 2 | 100 | | | C1 |

*1: A hydrogen-bonding functional group constitutes part of an acidic group as well.
*2: A mercapto group is also generated in the molecule by tautomerism.

TABLE 4

| | Tensile bonding strength [MPa]* | | Bonding durability [%] | Bonding material layer thickness [μm] |
|---|---|---|---|---|
| | Initial strength | Durable strength | | |
| Example 1 | 10.0 (0.2) | 2.0 (0.4) | 19 | 9 |
| Example 2 | 10.4 (1.2) | | | |
| Example 3 | 8.5 (1.4) | | | |
| Example 4 | 8.1 (0.8) | | | |
| Example 5 | 7.7 (0.6) | | | |
| Example 6 | 8.2 (0.9) | | | |
| Example 7 | 7.2 (0.4) | | | |
| Example 8 | 10.5 (0.5) | | | |
| Example 9 | 10.4 (0.8) | | | |
| Example 10 | 6.7 (0.4) | | | |
| Example 11 | 7.1 (0.3) | | | |
| Example 12 | 7.2 (0.4) | | | |
| Example 13 | 6.7 (0.3) | | | |
| Example 14 | 8.8 (0.8) | | | |
| Example 15 | 11.0 (0.5) | | | |
| Example 16 | 6.3 (0.9) | | | |
| Example 17 | 5.0 (0.6) | | | |
| Example 18 | 6.0 (0.5) | | | |
| Example 19 | 9.4 (0.4) | | | <1 |
| Example 20 | 9.4 (0.5) | | | <1 |
| Example 21 | 8.5 (0.7) | | | <1 |
| Example 22 | 9.0 (0.6) | | | <1 |
| Example 23 | 10.0 (0.4) | | | <1 |
| Example 24 | 12.5 (0.6) | | | |
| Example 25 | 12.5 (0.3) | | | |
| Example 26 | 12.7 (0.7) | | | |
| Example 27 | 10.5 (0.4) | 9.4 (0.6) | 90 | |
| Example 28 | 10.5 (0.6) | 8.2 (0.5) | 78 | |
| Example 29 | 9.9 (0.3) | 7.9 (0.5) | 79 | |
| Example 30 | 9.7 (0.6) | 7.8 (0.7) | 80 | |
| Example 31 | 12.6 (0.4) | 11.5 (0.8) | 91 | |
| Example 32 | 10.3 (0.4) | 7.8 (0.6) | 76 | |
| Example 33 | 10.0 (0.6) | 5.3 (0.4) | 53 | |
| Comparative Example 1 | 4.5 (0.9) | | | |
| Comparative Example 2 | 3.3 (0.3) | | | |
| Comparative Example 3 | 3.6 (0.8) | | | |
| Comparative Example 4 | 4.4 (0.6) | | | |
| Comparative Example 5 | 1.3 (0.2) | | | |

*Numerical values in the parentheses indicate standard deviations.

In the evaluation results shown in Table 4, in all of Examples 1 to 33, as compared to Comparative Examples 1 to 5, high initial tensile bonding strength was obtained.

When Examples 1 to 9, 15, 17, 18, and 24 to 31, in which bonding materials different from each other only in the composition of the polymerizable monomers were used, were compared, in each of Examples 1 to 6, 8, and 24 to 31, in which 5 parts by mass or more of the p2h1 type polymerizable monomer was blended, as compared to Examples 7, 17, and 18, in which less than 5 parts by mass of the p2h1 type polymerizable monomer was blended, high bonding strength was obtained. In addition, in each of Examples 1, 2, 8, and 24 to 31, in which the p2h1a1 type polymerizable monomer fell within the range of from 20 mass % to 50 mass % of all the polymerizable monomers, as compared to Examples 3 to 7, 9, 15, 17, and 18, in which the p2h1a1 type polymerizable monomer was less than 20 mass % or more than 50 mass % of all the polymerizable monomers, higher bonding strength was exhibited.

Further, in each of Examples 24 to 26 and 31, in which a coupling agent was blended, as compared to Examples 1 to 9, 15, 17, 18, and 27 to 30, in which no coupling agent was blended, high bonding strength was exhibited.

When comparison was performed within the group of Examples 1 and 16, in which bonding materials different from each other only in the blending amount of the volatile solvent were used, in Example 1, in which the blending amount of the volatile solvent fell within the range of from 10 parts by mass to 500 parts by mass with respect to 100 parts by mass of the polymerizable monomers, as compared to Example 16, in which the blending amount did not fall within the range of from 10 parts by mass to 500 parts by mass, high bonding strength was obtained. In addition, when comparison was performed within the group of Examples 7 and 10 to 13, in which bonding materials different from each other only in the blending amount of the volatile solvent were used, in each of Examples 7, 11, and 12, in which the blending amount of the volatile solvent fell within the range of from 50 parts by mass to 300 parts by mass with respect to 100 parts by mass of the polymerizable monomers, as compared to Example 13 and Example 10, in which the blending amount of the volatile solvent was less than 50 parts by mass and more than 300 parts by mass, respectively with respect to 100 parts by mass of the polymerizable monomers, high bonding strength was exhibited.

When Example 1 and Example 14, which were different from each other only in the kind of the volatile solvent, were compared, in Example 1, in which acetone, which was an aprotic solvent, was used, as compared to Example 14, in which IPA, which was a protic solvent, was used, higher bonding strength was exhibited.

When Examples 1 and 27 to 31, in which bonding materials different from each other only in the composition of the polymerizable monomers were used, were compared in teams of bonding durability, in each of Examples 27 to 31, in which the p1h1 type polymerizable monomer capable of generating a mercapto group in the molecule by tautomerism was blended, as compared to Example 1, in which the p1h1 type polymerizable monomer capable of generating a mercapto group in the molecule by tautomerism was not blended, high bonding durability was exhibited. Further, when Examples 27 to 30, which were different from each other in the kind of the p1h1 type polymerizable monomer capable of generating a mercapto group in the molecule by tautomerism, were compared, in Example 27, in which the functional group capable of generating a mercapto group by tautomerism was a thiouracil group, as compared to Examples 28 to 30, in which the functional group capable of generating a mercapto group by tautomerism was a functional group other than a thiouracil group, slightly high bonding durability was exhibited. In addition, in each of Examples 27 and 28, in which the polymerizable functional group of the p1h1 type polymerizable monomer capable of generating a mercapto group in the molecule by tautomerism was a (meth)acryloyl group, as compared to Examples 29 and 30, in which the polymerizable functional group was a vinyl group, slightly high initial tensile bonding strength was exhibited.

When Examples 1 and 19 to 22, which were different from each other only in the composition of the polymerization initiator, were compared, in each of Examples 19 to 22, in which part of the constituent components of (Bc) the chemical polymerization initiator was blended as (B) the polymerization initiator, as compared to Example 1, in which the photopolymerization initiator was used as (B) the polymerization initiator, the initial tensile bonding strength was slightly lowered but the bonding material layer thickness was reduced. When Examples 19 to 22 were compared in terms of initial tensile bonding strength, in each of Examples 19 and 20, in which the +IV-valent vanadium compound BMOV, which was a fourth-period transition metal compound, was blended as part of the constituent components of (Bc) the chemical polymerization initiator, as compared to Example 21, in which BPO, which was an organic peroxide, was blended, and Example 22, in which DEPT, which was a tertiary amine, was blended, high initial tensile bonding strength was exhibited.

When Examples 19 and 23, in which the same amount of BMOV was blended and bonding materials different from each other only in the composition of the polymerizable monomers were used, were compared, in Example 23, in which the p1h1 type polymerizable monomer having an acidic group in the molecule was blended, as compared to Example 19, in which the p1h1 type polymerizable monomer having an acidic group in the molecule was not blended, high bonding strength was exhibited.

When Examples 27, 32, and 33, in which the same bonding material was used and the first members were different from each other in the blending amount of the inorganic oxide, were compared, in Examples 27 and 32, in which the blending amount of the inorganic oxide in the first member was 15 mass % or more, as compared to Example 33, in which the blending amount was less than 15 mass %, high bonding durability was exhibited. In addition, in Example 27, in which the blending amount of the inorganic oxide in the first member was 25 mass % or more, as compared to Examples 32 and 33, in which the blending amount was less than 25 mass %, high bonding durability was exhibited.

The invention claimed is:

1. A bonding method, comprising:
a roughening adherend surface step comprising roughening an adherend surface of a member containing polyaryletherketone resin composite material, which contains a polyaryletherketone resin and an inorganic oxide;
a bonding material-applying step comprising applying, onto the roughened adherend surface of the member containing polyaryletherketone resin composite material, a bonding material containing (A) polymerizable monomers and at least a part of constituent components of (B) a polymerization initiator, in which, based on total mass of all polymerizable monomers, a content of (p2) a polymerizable monomer having at least two or more polymerizable functional groups in a molecule is 50 mass % or more, and a content of (p1h1) a polymerizable monomer having at least one or more polymerizable functional groups and one or more hydrogen-bonding functional groups in a molecule is 5 mass % or more;
a curing step comprising curing the bonding material;
wherein (p1h1) the polymerizable monomer having at least one or more polymerizable functional groups and one or more hydrogen-bonding functional groups in a molecule further contains
a p1h1 type polymerizable monomer containing sulfur selected from the group consisting of (i) a polymerizable monomer having a permanently present mercapto group in the molecule, (ii) a polymerizable monomer having a mercapto group generated in the molecule by tautomerism, and (iii) a polymerizable monomer having a mercapto group generated in the molecule by a stimulus reaction, and
wherein, based on total mass of all the polymerizable monomers, a content of the p1h1 type polymerizable monomer containing sulfur is 0.005 mass % or more and 10 mass % or less.

2. The bonding method according to claim 1, wherein the inorganic oxide is selected from the group consisting of silica, silica-titania, and silica-zirconia.

3. The bonding method according to claim 1, wherein the bonding material contains (C) a volatile solvent.

4. The bonding method according to claim 1, wherein the bonding material contains (D) a coupling agent having at least one or more first reactive groups each capable of reacting with the inorganic oxide, and one or more second reactive groups each capable of reacting with an organic compound.

5. The bonding method according to claim 2, wherein the bonding material contains (D) a coupling agent having at least one or more first reactive groups each capable of reacting with the inorganic oxide, and one or more second reactive groups each capable of reacting with an organic compound.

6. The bonding method according to claim 1,
wherein (B) the polymerization initiator comprises at least (Bc) a chemical polymerization initiator, and the bonding material contains part of constituent components of (Bc) the chemical polymerization initiator, and
wherein the curing step is initiated by carrying out a contact step of bringing the bonding material into contact with a polymerization auxiliary material containing a remainder constituent component of (Bc) the chemical polymerization initiator.

7. The bonding method according to claim 2,
wherein (B) the polymerization initiator comprises at least (Bc) a chemical polymerization initiator, and the bonding material contains part of constituent components of (Bc) the chemical polymerization initiator, and
wherein the curing step is initiated by carrying out a contact step of bringing the bonding material into contact with a polymerization auxiliary material containing a remainder constituent component of (Bc) the chemical polymerization initiator.

* * * * *